US007557235B2

(12) United States Patent
Lai et al.

(10) Patent No.: US 7,557,235 B2
(45) Date of Patent: Jul. 7, 2009

(54) HYDROXYL-TERMINATED THIOCARBONATE CONTAINING COMPOUNDS, POLYMERS, AND COPOLYMERS, AND POLYURETHANES AND URETHANE ACRYLICS MADE THEREFROM

(75) Inventors: John Ta-Yuan Lai, Broadview Heights, OH (US); Ronald P. Shea, Akron, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 526 days.

(21) Appl. No.: 10/913,972

(22) Filed: Aug. 6, 2004

(65) Prior Publication Data

US 2005/0009999 A1   Jan. 13, 2005

Related U.S. Application Data

(63) Continuation-in-part of application No. 10/681,679, filed on Oct. 8, 2003, now Pat. No. 7,335,788, which is a continuation-in-part of application No. 10/278,335, filed on Oct. 23, 2002, now Pat. No. 7,205,368, which is a continuation-in-part of application No. 09/505,749, filed on Feb. 16, 2000, now Pat. No. 6,596,899, application No. 10/913,972, which is a continuation-in-part of application No. 10/219,403, filed on Aug. 15, 2002, now Pat. No. 6,894,116.

(51) Int. Cl.
C07C 329/00 (2006.01)
C08G 75/00 (2006.01)
(52) U.S. Cl. .................. 558/243; 558/244; 558/245; 558/248; 525/535
(58) Field of Classification Search ......... 558/243–245, 558/248; 525/535
See application file for complete search history.

(56) References Cited

U.S. PATENT DOCUMENTS

| 3,285,945 | A | 11/1966 | Wember |
| 3,285,949 | A | 11/1966 | Siebert |
| 3,770,698 | A | 11/1973 | Riew |
| 3,860,641 | A | 1/1975 | Zengel et al. |
| 3,928,491 | A | 12/1975 | Waters |
| 3,992,432 | A | 11/1976 | Napier et al. |
| 4,769,419 | A | 9/1988 | Dawdy |
| 5,055,515 | A | 10/1991 | Backderf |
| 5,140,068 | A | 8/1992 | Siebert et al. |
| 5,157,077 | A | 10/1992 | Siebert et al. |
| 5,198,510 | A | 3/1993 | Siebert et al. |
| 5,258,445 | A | 11/1993 | Sperk, Jr. et al. |
| 5,280,068 | A | 1/1994 | Siebert et al. |
| 5,312,956 | A | 5/1994 | Bertsch |
| 5,385,963 | A | 1/1995 | McBain et al. |
| 6,153,705 | A | 11/2000 | Corpart et al. |
| 6,380,335 | B1 | 4/2002 | Charmot et al. |
| 6,395,850 | B1 | 5/2002 | Charmot et al. |
| 6,545,098 | B1 | 4/2003 | Bouhadir et al. |
| 6,596,899 | B1 | 7/2003 | Lai |

FOREIGN PATENT DOCUMENTS

| EP | 0713132 | 5/1996 |
| GB | 1223524 | 2/1971 |
| WO | 98/01478 | 1/1998 |
| WO | 99/05099 | 2/1999 |
| WO | 99/31144 | 6/1999 |
| WO | 99/35177 | 7/1999 |
| WO | 2004037780 | 5/2004 |

OTHER PUBLICATIONS

World Polymer Congress, 37th International Symposium on Macromolecules, Jul. 12-17, 1998, Gold Coast, Australia, pp. 1-10.

"Living Free-Radical Polymerization by Reversible Addition-Fragmentation Chain Transfer: The RAFT Process", John Chiefari, et al., *CSIRO Molecular Science, Bag 10*, Clayton South. Clayton, Victoria 3169, Australia, Received Mar. 27, 1998, Revised Manuscript Received Jun. 10, 1998.

"The Synthesis of Organic Trethiocarbonates<sup>1</sup>", H.C. Godt, Jr., and R.E. Wann, *Journal of Organic Chemisry*, vol. 26, pp. 4047-4050, 1961.

"Phase-Transfer Synthesis of Symmetrical and Unsymmetrical Dialkyl Trithiocarbonates", Lacopo Degani, et al, *Synthesis*, pp. 894-899, 1986.

"A New Form of Controlled Growth Free Radical Polymerization", Julia Kristina, et al., CSIRO, Division of Chemicals and Polymers, *Macromol, Symp.* 111, pp. 13-23, 1996.

"One Pot Transfer Synthesis of Trithiocarbonates from Carbon Disulphide and Alkyl Halides", Albert W.M. Lee, et al, *Synthetic Comm.*, vol. 18, No. 13, pp. 1531-1536, 1988.

"A Novel One-step Synthesis of Symmetrical Dialkyl Trithiocarbonates", Man-kit Leung, et al, *Journal of Chemical Research (S)*, 1995, pp. 478-479.

"Direct Synthesis of Double Hydrophilic Statistical di- and Triblock Copolymers Comprised of Acrylamide and Acrylic Acid Units via the MADIX Process", Daniel Taton, et al, Macromolecular, Rapid Communication, vol. 22, No. 18, pp. 1497-1503, 2001.

"Dithiocarbamates As Universal Reversible Addition-Fragmentation Chain Transfer Agents", M. Destarac, et al, Macromolecular Rapid Communication, vol. 21, No. 15, pp. 1035-1039, 2000.

(Continued)

*Primary Examiner*—Taylor Victor Oh
(74) *Attorney, Agent, or Firm*—Thoburn T. Dunlap

(57) ABSTRACT

Carboxylate terminated thiocarbonates are reacted with a polyfunctional alcohol to form a hydroxyl-terminated thiocarbonate compound.

9 Claims, No Drawings

OTHER PUBLICATIONS

"Living Radical Polymerization with Reversible Addition—Fragmetation Chain Transfer (RAFT Polymerization) Using Ditriocarbamates as Chain Transfer Agents", Roshan T.A. Mayadunne, et al., Macromoelcules, vol. 32, pp. 6977-6980, 1999.

Yusuf Yagci et al., *Progress in Polymer Science*, "Light-Induced Synthesis Of Block And Graft Copolymers", vol. 15, pp. 551-601, 1990.

*Polymer Handbook, Third Edition*, J. Brandup et al., John Wiley: New York, "6. Peresters and Peroxy Carbonates", pp. 11/53, 1989.

"The Chemistry of Free Radical Polymerization", Moad and Solomon, Pergamon, London, pp. 53-95, 1995.

"Telechelic Polymers: Synthesis and Applications", Eric J. Goethe, CRC Press, Boca Raton, Florida, Chapter 4—Telechelics By Free Radical Polymerization Reactions, pp. 61-94, and Chapter 10—Terminal Transformation Of Telechelics, pp. 229-259, 1989.

A. Bistrzycki, et al., "Synthesis Of Derivatives Of 1,3-Ox[a]thiophane" *Helvetica Chimica Acta*, vol. 3, 1920, pp. 447-467.

C.W. Pluijgers, et al., "Plant Growth-Regulating Activity Of S-Carboxymethyl-N,N-Dimethyldithiocarbamate And Related Compounds", *Recueil Des Travaux Chimiques Des Pays-Bas*, vol. 80, No. 9/10, Sep. 9, 1961, pp. 1089-1100.

L. Field, et al., "Preparation And Chlorinolysis Of β-Mercaptodiethylacetic Acid", *Journal of the American Chemical Society6*, vol. 74, No. 18, Sep. 20, 1952, pp. 4707-4708.

F. Andreani, et al., "New α-Substituted Arylthioacetic Derivatives Forming Analogues Of Clofibrate", *IL Farmaco, Edizione Scientifica*, vol. 30, No. 10, Oct. 1975, pp. 847-858.

R.J. Stoodley, "Studies Related to Penicillins. Part II. The Rearrangement of 6-β-Aminopencillanic Acid to 2,3-Dihydro-6-methoxycarbonyl-2,2-dimethyl-1,4-thiazin-3-one", *Journal of the Chemical Society*, Section C: Organic Chemistry, No. 23, 1968, pp. 2891-2894.

HYDROXYL-TERMINATED THIOCARBONATE CONTAINING COMPOUNDS, POLYMERS, AND COPOLYMERS, AND POLYURETHANES AND URETHANE ACRYLICS MADE THEREFROM

CROSS-REFERENCE

This patent application is a continuation-in-part application based on U.S. application Ser. No. 10/681,679 filed Oct. 8, 2003, now U.S. Pat. No. 7,335,788 for S-(α,α'-Disubstituted-α"-Acetic Acid) Substituted Dithiocarbonate Derivatives for Controlled Radical Polymerizations, Process and Polymers Made Therefrom, which is a continuation-in-part application based on U.S. application Ser. No. 10/278,335, filed Oct. 23, 2002 now U.S. Pat. No. 7,205,368 for S-(α,α'-Disubstituted-α"-Acetic Acid) Substituted Dithiocarbonate Derivatives for Controlled Radical Polymerizations, Process and Polymers Made Therefrom which in turn is a continuation-in-part based on U.S. application Ser. No. 09/505,749 filed Feb. 16, 2000, now U.S. Pat. No. 6,596,899 issued Jul. 22, 2003, for S,S'-Bis-(α,α'-Disubstituted-α"-Acetic Acid)—Trithiocarbonates And Derivatives As Initiator—Chain Transfer Agent—Terminator For Controlled Radical Polymerizations And The Process For Making The Same. This application is also a continuation-in-part based upon U.S. application Ser. No. 10/219,403 filed Aug. 15, 2002 now U.S. Pat. No. 6,894,116 for S,S'-Bis-(α,α'-Disubstituted-α"-Acetic Acid)—Trithiocarbonates and Polymers Thereof For Toughening Thermosetting Resins.

FIELD OF THE INVENTION

Hydroxyl-terminated thiocarbonate containing compounds (HTT) are utilized to form polymers and copolymers useful for numerous applications. HTT are utilized to form hydroxyl terminated polymers or copolymers which are used in one embodiment to form thermoplastic polyurethane in bulk. Waterborne polyurethane dispersions are also formed utilizing HTT. In yet another embodiment, solvent based polyurethanes are described. The bulk, dispersion, and solvent based urethanes can contain acrylic repeat units. Various methods are also described for preparing the various thiocarbonate containing polymers and copolymers of the present invention.

BACKGROUND OF THE INVENTION

U.S. Pat. No. 6,596,899 issued Jul. 22, 2003 relates to a s,s'-bis-α,α'-disubstituted-α"-acetic acid)—trithiocarbonate and derivatives thereof can be used as an initiator, chain transfer agent, or terminator for polymerization of monomers such as free radical polymerizable monomers. Homopolymers, copolymers, and the like as well as block copolymers can be made utilizing the trithio carbonate compound such as in a living free radical polymerization as well as to form telechelic polymers.

U.S. patent application Ser. No. 10/219,403 filed Aug. 15, 2002 relates to a toughener comprising a trithiocarbonate polymer having an epoxy end group which is utilized with various thermosettable polymers such as epoxy, polyurethane, and the like. A toughened composition is made by curing the thermosettable polymer and the toughener utilizing various curing agents. U.S. application Ser. No. 10/219,403 is hereby fully incorporated by reference.

U.S. patent application Ser. No. 10/278,335 filed Oct. 23, 2002 and Ser. No. 10/681,679 filed Oct. 8, 2003 relate to dithiocarbonate derivatives, along with a process for preparing the same. The dithiocarbonate compounds can be utilized as initiators, chain transfer agents and/or terminators in controlled free radical polymerizations. The dithiocarbonates can also be used to produce polymers having a narrow molecular weight distribution. These compounds can also introduce functional groups into the resulting polymers. The dithiocarbonate compounds have low odor and are substantially colorless. U.S. application Ser. Nos. 10/278,335 and 10/681,679 are hereby fully incorporated by reference.

Telechelic di-functional hydroxyl-terminated vinyl polymers are generally not readily available, especially hydroxyl-terminated acrylate polymers.

SUMMARY OF THE INVENTION

In one embodiment, carboxylate-terminated di- or trithiocarbonates are reacted with a polyfunctional alcohol such as a diol or other polyol to form hydroxyl terminated di- or trithiocarbonates. In a further embodiment, one or more monomers, which are the same or different, are reacted into the backbone of the thiocarbonate compound either before or after reaction with the polyol.

The hydroxyl terminated thiocarbonate containing polymers or copolymers are reacted through the hydroxyl groups along with optional isocyanate reactive compounds, with a mono or desirably a polyisocyanate compound to form a thermoplastic or thermoset polyurethane. The urethane can be prepared in bulk, solvent or be an aqueous dispersion and optionally contain an acrylic copolymer.

DETAILED DESCRIPTION OF THE INVENTION

Thiocarbonate Compounds

The thiocarbonate compounds utilized in the present invention are preferably polythiocarbonates such as dithiocarbonate or trithiocarbonate compounds and derivatives thereof. By the term "thiocarbonate" it is meant a compound having at least one segment having the formula

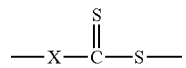

where "x" comprises OR, SR, or NR, with R being various hydrocarbon, hetero atom and/or hydrogen containing structures or the like as illustrated hereinbelow, but not limited thereto.

Suitable trithiocarbonate compounds for use in the present invention, but not limited thereto, are disclosed in U.S. Pat. No. 6,596,899 to Lai, and U.S. patent application Ser. No. 10/219,403, filed Aug. 15, 2002, both hereby fully incorporated by reference including the preparation thereof. In one embodiment, trithiocarbonate compounds have the following general formula:

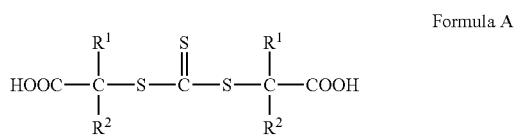

Formula A wherein $R^1$ and $R^2$, independently, is the same or different, and is a linear or branched alkyl having from 1 to about 6 carbon atoms, or a $C_1$ to about $C_6$ alkyl having one or more substituents, or one or more aryls or a substituted aryl group having 1 to 5 substituents on the aryl ring, where the one or more substituents, independently, comprise an alkyl having from 1 to 6 carbon atoms; or an aryl; or a halogen such as fluorine or chlorine; or a cyano group; or an ether having a total of from 2 to about 20 carbon atoms such as methoxy, or hexanoxy; or a nitro; or combinations thereof. Examples of such compounds include s,s'-bis-2-methyl-2-propanoic acid-trithiocarbonate and s,s'-bis-(2-phenyl-2-propanoic acid)-trithio-carbonate. $R^1$ and $R^2$ can also form or be a part of a cyclic ring having from 5 to about 12 total carbon atoms. $R^1$ and $R^2$ are preferably, independently, methyl or phenyl groups.

The abbreviated reaction formula for one method for the preparation of s,s'-bis-($\alpha,\alpha'$-disubstituted-$\alpha''$-acetic acid)-trithiocarbonates is generally written as follows:

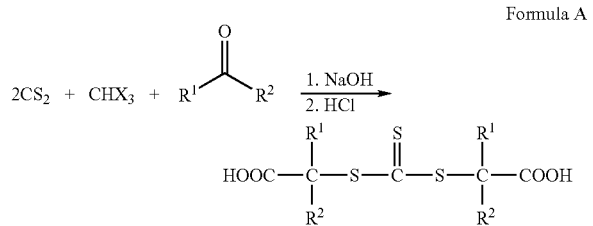

Formula A where "x" is halogen and $R^1$ and $R^2$ are the same as set forth above.

The process utilized to form s,s'-bis-($\alpha,\alpha'$-disubstituted-$\alpha''$-acetic acid)-trithiocarbonate compounds is generally a multi-step process and includes combining the carbon disulfide and a base whereby an intermediate trithio structure is formed. Ketone can serve as solvent for the carbon disulfide/base reaction and thus can be added in the first step of the reaction. In the second step of the reaction, the haloform, or haloform and ketone, or a $\alpha$-trihalomethyl-$\alpha$-alkanol are added to the trithio intermediate mixture and reacted in the presence of additional base. The formed reaction product, is subsequently acidified, thus completing the reaction and forming the above described s,s'-bis-($\alpha,\alpha'$-disubstituted-$\alpha''$-acetic acid)-trithiocarbonate compound.

Another aspect of present invention utilizes trithiocarbonate compounds having the following formula:

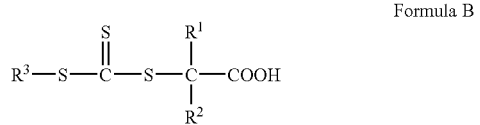

Formula B wherein $R^3$ comprises a benzyl group, $C_1$-$C_{18}$ alkyl, or substituted alkyl such as halogen, hydroxyl, or alkoxy, $C_1$-$C_{18}$ hydroxyalkyl, aralkyl, cyanoalkyl, aminoalkyl, carboxylalkyl, carboalkoxyalkyl or mercaptoalkyl, and $R^1$ and $R^2$ are defined hereinabove. The resulting compound is an s-substituted-s'-($\alpha,\alpha'$-disubstituted-$\alpha''$-acetic acid)-trithiocarbonate.

Dithiocarbonate compounds which are utilized in some embodiments of the present invention are disclosed in U.S. application Ser. No. 10/278,335 filed Oct. 23, 2002 and U.S. application Ser. No. 10/681,679 filed Oct. 8, 2003, herein fully incorporated by reference including the preparation thereof. In one embodiment the dithiocarbamate compounds have the following formula:

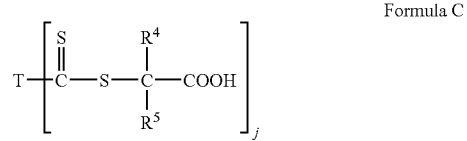

Formula C wherein j is 1 or 2, with the proviso that when j is 1, T is $-(NR^6R^7)$; and when j is 2, T is a divalent radical having a nitrogen atom directly connected to each carbon atom of the two thiocarbonyl groups present;

wherein $R^4$ and $R^5$, independently, is the same or different, is optionally substituted, and is a linear or branched alkyl having from 1 to about 6 or about 12 carbon atoms; or an aryl group having from 6 to about 18 carbon atoms, optionally containing heteroatoms;

wherein the $R^4$ and/or $R^5$ substituents, independently, comprise an alkyl having from 1 to 6 carbon atoms; an aryl group; a halogen; a cyano group; an ether having a total of from 2 to about 20 carbon atoms; a nitro; or combinations thereof. $R^4$ and $R^5$ can also form or be a part of a substituted or unsubstituted cyclic ring having from 3 to about 12 total carbon atoms wherein the substituents are described above. $R^4$ and $R^5$ are preferably, independently, methyl or phenyl groups;

wherein $R^6$ and $R^7$, independently, is the same or different, optionally is substituted, optionally contains heteroatoms; and is hydrogen; a linear or branched alkyl having from 1 to about 18 carbon atoms, an aryl group having from about 6 to about 18 carbon atoms optionally saturated or unsaturated; an arylalkyl having from about 7 to about 18 carbon atoms; an alkenealkyl having from 3 to about 18 carbon atoms; or derived from a polyalkylene glycol ether having from 3 to about 200 carbon atoms. $R^6$ and $R^7$ can also be derived from amines such as, but not limited to, piperazine, morpholine, pyrrolidine, piperidine, 4-alkyl amino-2,2,6,6-tetramethyl piperid ine, 1-alkylamioalkyl-3,3,5,5-tetramethyl-2-piperazinone, hexamethyleneimine, phenothiazine, iminodibenzyl, phenoxazine, N,N'-diphenyl-1,4-phenylenediamine, dicyclohexylamine and derivatives thereof. $R^6$ and $R^7$ can also form a substituted or unsubstituted cyclic ring, optionally containing heteroatoms, along with the nitrogen having a total of from 4 to about 12 carbon atoms, such as benzotriazole, tolyltriazole, imidazole, 2-oxazolidone, 4,4-dimethyloxazolidone and the like. The $R^6$ and $R^7$ substituents, independently, can be the same as described herein with respect to $R^{13}$ as set forth herein below. $R^6$ and $R^7$ are preferably, independently, a phenyl group or an alkyl or substituted alkyl having from 1 to about 18 carbon atoms such as a methyl group, or $R^6$ and $R^7$, independently, are hexamethylene.

In Formula C, when j is 2, the dithiocarbamate compound is a bis-S-($\alpha,\alpha'$-disubstituted-$\alpha''$-acetic acid) dithiocarbamate having the following formula:

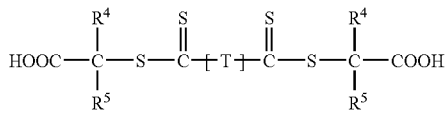

wherein $R^4$ and $R^5$ are defined hereinabove; and wherein T is a divalent bridging radical having a nitrogen atom directly connected to each of the thiocarbonyl groups present.

When j is 1, T of above formula is $(NR^6R^7)$ and the dithiocarbamate compound is a S-(α,α'-disubstituted-α"-acetic acid) dithiocarbamate generally having the following formula:

Formula D

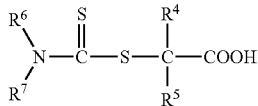

wherein $R^4$, $R^5$, $R^6$, and $R^7$ are as defined hereinabove.

When j is 2, T is:

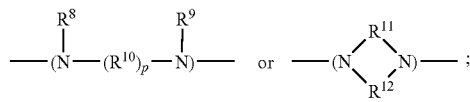

wherein $R^8$ and $R^9$, independently, is the same or different, is optionally substituted, and is hydrogen, a linear or branched alkyl having from 1 to about 18 carbon atoms, an aryl group having from about 6 to about 18 carbon atoms, an arylalkyl having from 7 to about 18 carbon atoms, an alkenealkyl having from 3 to about 18 carbon atoms, wherein the substitutents can be the same as described herein for $R^1$ and $R^2$;

wherein $R^{10}$ is optionally substituted, and is an alkylene group having from 1 to about 18 carbon atoms with about 1 to about 6 carbon atoms preferred, or derived from a polyalkylene glycol ether having from 3 to about 200 carbon atoms, wherein the substituents can be the same as described herein for $R^1$ and $R^2$ or are heteroatoms such as oxygen, nitrogen, sulfur or phosphorous; p is 0 or 1; and wherein $R^{11}$ and $R^{12}$ independently, is the same or different, and is optionally substituted as described for $R^1$ and $R^2$, and is an alkylene group having from 1 to about 4 carbon atoms, with $R^{11}$ and $R^{12}$ preferably having a collective total of 3 to 5 carbon atoms.

In further embodiments, T is:

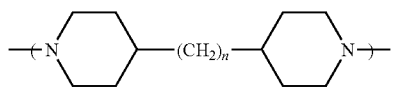

wherein n is 0 to about 18, with 0 to about 6 preferred;

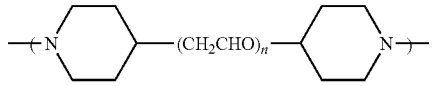

wherein n is 0 to about 18, with 0 to about 6 preferred;

Some specific non-limiting examples of T bridging radicals are:

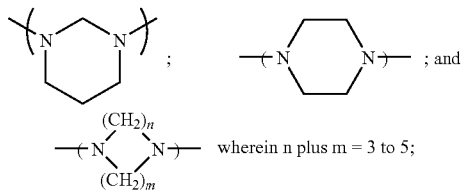

The S-(α,α'-disubstituted-α"-acetic acid) or bis S-(α,α'-disubstituted-α"-acetic acid) dithiocarbamates are generally a reaction product of a metal salt of a dithiocarbamate (can be generated in situ from amine, carbon disulfide and metal hydroxide), a haloform, and a ketone. A phase transfer catalyst, solvent, and a base such as sodium hydroxide or potassium hydroxide can also be utilized to form the S-(α,α'-disubstituted-α"-acetic acid) or bis S-(α,α'-disubstituted-α"-acetic acid) dithiocarbamates.

It is to be understood throughout the application formulas, reaction schemes, mechanisms, etc., and the specification that metals such as sodium or bases such as sodium hydroxide are referred to and the application of the present invention is not meant to be solely limited thereto. Other metals or bases such as, but not limited to, potassium and potassium hydroxide, respectively, are contemplated by the disclosure of the present invention.

Alkoxy dithiocarbonate compounds are utilized in some embodiments of the present invention which have the following general formula:

Formula E

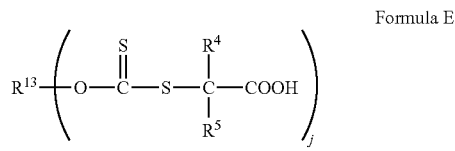

wherein j=1 or 2,
wherein $R^4$ and $R^5$ are as defined hereinabove;
wherein $R^{13}$ is optionally substituted, and can be a linear or branched alkyl or alkylene having from 1 to about 12 carbon atoms; an aryl group, optionally saturated or unsaturated; an arylalkyl having from 7 to about 18 carbon atoms; an acyl group; an alkenealkyl having from 3 to about 18 carbon atoms; an alkene group; an alkylene group; an alkoxyalkyl; derived from a polyalkylene glycol; derived from a polyalkylene glycol monoalkyl ether having from 3 to 200 carbon atoms; derived from a polyalkylene glycol monoaryl ether having from 3 to 200 carbon atoms; a polyfluoroalkyl such as 2-trifluoroethyl; a phosphorous containing alkyl; or a substituted or unsubstituted aryl ring containing heteroatoms. Alkyl and alkylene groups from 1 to 6 carbon atoms are preferred; wherein the $R^{13}$ substituents comprise an alkyl having from 1 to 6 carbon atoms; an aryl; a halogen such as fluorine or chlorine; a cyano group; an amino group; an alkene group; an alkoxycarbonyl group; an aryloxycarbonyl group; a carboxy group; an acyloxy group; a carbamoyl group; an alkylcarbonyl group; an alkylarylcarbonyl group; an arylcarbonyl group; an arylalkylcarbonyl group; a phthalimido group; a maleimido group; a succinimido group; amidino group; guanidimo group; allyl group; epoxy group; alkoxy group; an alkali metal salt; a cationic substitutent such as a quaternary ammonium salt; a hydroxyl group; an ether having a total of from 2 to about 20 carbon atoms such as methoxy, or hexanoxy; a nitro; sulfur; phosphorous; a carboalkoxy group; a heterocyclic group containing one or more sulfur, oxygen or nitrogen atoms, or combinations thereof; and wherein "a" is 1 to about 4 with 1 or 2 preferred.

The compounds of the above formula are generally identified as O-alkyl-S-($\alpha,\alpha'$-disubstituted-$\alpha''$-acetic acid) xanthates. The O-alkyl-S-($\alpha,\alpha'$-disubstituted-$\alpha''$-acetic acid) xanthates are generated as the reaction product of an alkoxylate salt, carbon disulfide, a haloform, and a ketone. Alternatively, a metal salt of xanthate can be utilized in place of the alkoxylate salt and carbon disulfide.

The general reaction mechanism for forming the O-alkyl-S-($\alpha,\alpha'$-disubstituted-$\alpha''$-acetic acid) xanthates is as follows:

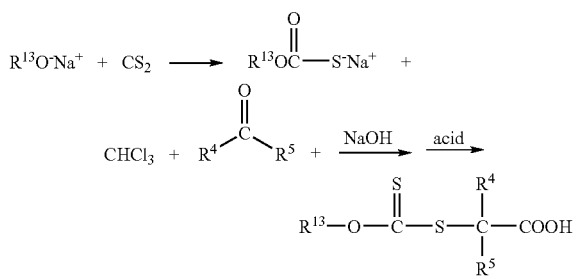

It is to be understood that while a few specific thiocarbonate compounds have been described herein, the present invention is not limited to such compounds.

The various thiocarbonate compounds including the various trithiocarbonates and the various dithiocarbonates are prepared in a manner as set forth in the above noted U.S. Pat. No. 6,596,899 granted Jul. 22, 2003; U.S. application Ser. No. 10/219,403 filed Aug. 15, 2002; U.S. application Ser. No. 10/278,335 filed Oct. 23, 2002; and U.S. application Ser. No. 10/681,679 filed Oct. 8, 2003, all of which are hereby fully incorporated by reference with regard to reaction conditions including temperature, type and amount of catalysts, and the like.

Hydroxyl Terminated Thiocarbonate Compounds, Polymers and Copolymers

The acid group terminated thiocarbonate compounds are reacted with a polyfunctional alcohol such as a diol or other polyol to form various hydroxyl terminated thiocarbonate compounds. Accordingly, monohydroxyl thiocarbonates, and dihydroxy thiocarbonates or other polyol compounds are formed.

Suitable polyols which are reacted with the thiocarbonate compounds have the formula:

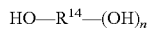

wherein, the hydroxyl groups are not attached to the same carbon atom, and wherein n is 1 to 7 and preferably is 1. $R^{14}$ can preferably be part of at least one simple or substantially hydrocarbon polyol, or less desirably part of at least one complex polyol. $R^{14}$ is an alkyl or substituted alkyl or alkylene group having 2 to 200 carbon atoms and desirably from 2 to about 10 carbon atoms. The hydroxyl groups can be at the terminals of a main chain, or a branched chain, or a cyclic chain. The substituted alkyl or alkylene can contain oxygen, ether, ester, sulfide, halide, cyano and any heterocyclic rings including carbohydrates.

The so-called simple or substantially hydrocarbon polyhydroxyl compounds are highly preferred and have alkyl or alkylene groups with the substituted alkyl or alkylene groups containing oxygen or a halide. Specific examples include ethylene glycol, 1,2- and 1,3-propylene glycols, 1,2-, 1,3-, 1,4-, and 2,3-butylene glycols, hexane diols, neopentyl glycol, 1,6-hexanediol, 1,8-octanediol, and other glycols such as bisphenol-A, cyclohexane diol, cyclohexane dimethanol (1,4-bis-hydroxymethylcyclohexane), 2-methyl-1,3-propanediol, 2,2,4-trimethyl-1,3-pentanediol, diethylene glycol, triethylene glycol, tetraethylene glycol, polyethylene glycol, dipropylene glycol, polypropylene glycol, dibutylene glycol, polybutylene glycol, dimerate diol, trimethylol propane, pentaerythritol, hydroxylated bisphenols, halogenated diols, and the like, and mixtures thereof. Highly preferred diols include ethylene glycol, diethylene glycol, propylene glycol, trimethylolpropane, butylene glycol, hexane diol, and neopentyl glycol.

Examples of complex polyols which are not desired but can be utilized include higher polymeric polyols such as polyester polyols and polyether polyols, as well as polyhydroxy polyester amides, hydroxyl-containing polycaprolactones, hydroxyl-containing acrylic interpolymers, hydroxyl-containing epoxides, polyhydroxy polycarbonates, polyhydroxy polyacetals, polyhydroxy polythioethers, polysiloxane polyols, ethoxylated polysiloxane polyols, polybutadiene polyols and hydrogenated polybutadiene polyols, polyacrylate polyols, halogenated polyesters and polyethers, and the like, and mixtures thereof. The polyester polyols, polyether polyols, polycarbonate polyols, polysiloxane polyols, polyacetals, and ethoxylated polysiloxane polyols are preferred.

The polyester polyols typically are esterification products prepared by the reaction of organic polycarboxylic acids or their anhydrides with a stoichiometric excess of a diol. Examples of suitable polyols for use in the reaction include poly(glycol adipate)s, poly(ethylene terephthalate) polyols, polycaprolactone polyols, orthophthalic polyols, sulfonated and phosphonated polyols, and the like, and mixtures thereof.

The diols used in making the polyester polyols include alkylene glycols having from 2 to about 20 total carbon atoms, e.g., ethylene glycol, 1,2- and 1,3-propylene glycols, 1,2-, 1,3-, 1,4-, and 2,3-butylene glycols, hexane diols, neopentyl glycol, 1,6-hexanediol, 1,8-octanediol, and other glycols such as bisphenol-A, cyclohexane diol, cyclohexane dimethanol (1,4-bis-hydroxymethylcyclohexane), 2-methyl-1,3-propanediol, 2,2,4-trimethyl-1,3-pentanediol, diethylene glycol, triethylene glycol, tetraethylene glycol, polyethylene glycol, dipropylene glycol, polypropylene glycol, dibutylene glycol, polybutylene glycol, dimerate diol, Trimethylol propane, pentaerythritol hydroxylated bisphenols, polyether glycols, halogenated diols, and the like, and mixtures thereof. Highly preferred diols include ethylene glycol, diethylene glycol, butylene glycol, hexane diol, and neopentyl glycol.

Suitable carboxylic acids used in making the polyester polyols generally have from 1 to about 20 total carbon atoms and include dicarboxylic acids and tricarboxylic acids and anhydrides, e.g., maleic acid, maleic anhydride, succinic acid, glutaric acid, glutaric anhydride, adipic acid, suberic acid, pimelic acid, azelaic acid, sebacic acid, chlorendic acid, 1,2,4-butane-tricarboxylic acid, phthalic acid, the isomers of phthalic acid, phthalic anhydride, fumaric acid, dimeric fatty acids such as oleic acid, and the like, and mixtures thereof. Preferred polycarboxylic acids used in making the polyester polyols include aliphatic or aromatic dibasic acids.

The preferred polyester polyol is a diol. Preferred polyester diols include poly(butanediol adipate); hexane diol adipic acid and isophthalic, acid polyesters such as hexane adipate isophthalate polyester; hexane diol neopentyl glycol adipic acid polyester diols, e.g., Piothane 67-3000 HNA (Panolam Industries) and Piothane 67-1000 HNA; as well as propylene glycol maleic anhydride adipic acid polyester diols, e.g., Piothane 50-1000 PMA; and hexane diol neopentyl glycol fumaric acid polyester diols, e.g., Piothane 67-500 HNF. Other preferred polyester diols include Rucoflex® S1015-35, S1040-35, and S-1040-110 (Bayer Corporation.

Polyether diols may be substituted in whole or in part for the polyester diols. Polyether polyols contain from 2 to about 15 carbon atoms in the repeat unit and are obtained in known manner by the reaction of (A) the starting compounds that contain reactive hydrogen atoms, such as water or the diols set forth for preparing the polyester polyols, and (B) alkylene oxides, such as ethylene oxide, propylene oxide, butylene oxide, styrene oxide, tetrahydrofuran, epichlorohydrin, and the like, and mixtures thereof. Preferred polyethers include poly(propylene glycol), polytetrahydrofuran, and copolymers of poly(ethylene glycol) and poly(propylene glycol).

Polycarbonates include those obtained from the reaction of (A) diols such 1,3-propanediol, 1,4-butanediol, 1,6-hexanediol, diethylene glycol, triethylene glycol, tetraethylene glycol, and the like, and mixtures thereof with (B) diarylcarbonates such as diphenylcarbonate or phosgene.

Polyacetals include the compounds that can be prepared from the reaction of (A) aldehydes, such as formaldehyde and the like, and (B) glycols such as diethylene glycol, triethylene glycol, ethoxylated 4,4'-dihydroxy-diphenyldimethylmethane, 1,6-hexanediol, and the like. Polyacetals can also be prepared by the polymerization of cyclic acetals.

Polysiloxanes include polydialkylsiloxane diols wherein the alkyl group has from 1 to about 3 carbon atoms such as polydimethylsiloxane diol made by GE such as OSI-14209, and by GEL-EST such as DMS-C21.

The aforementioned diols useful in making polyester polyols can also be used as additional reactants to prepare the isocyanate terminated prepolymer.

The hydroxyl terminated thiocarbonate compounds are formed by combining the desired thiocarbonate and base diol or polyol in a suitable reaction vessel. The reaction is an esterification and the same is known to the art and to the literature. For example, usually an acid catalyst such as p-toluenesulfonic acid is utilized and a reaction temperature is from about 20° C. to about 200° C. and preferably from about 80° C. to about 150° C. The number of repeat units derived from the thiocarbonate compounds in the hydroxyl terminated thiocarbonate compositions ranges generally from about 1 to about 20, and desirably from about 1 to about 10.

For example, a general reaction mechanism for preparing a trithiocarbonate diol is:

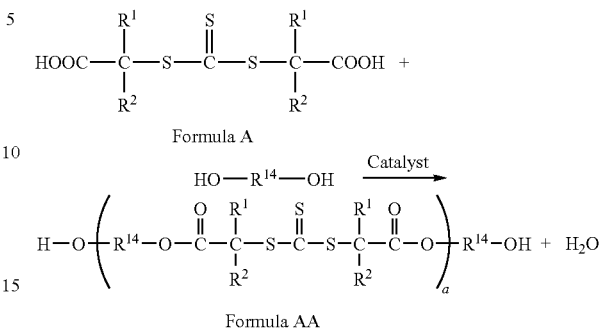

wherein "a" is from about 1 to about 10 or about 20, and desirably from about 1 to about 5, and $R^1$, $R^2$ and $R^{14}$ are defined herein above. The number of repeat groups "a" will vary depending upon the equivalent ratio of hydroxyl groups to carboxylic acid groups. Thus, when the OH/COOH ratio is preferably about 2 or greater, generally about one "a" unit will predominate, and the product can be a mixture of different "a" numbers.

A general reaction mechanism for preparing a trithiocarbonate polyol utilizing the trithiocarbonate of Formula B is as follows.

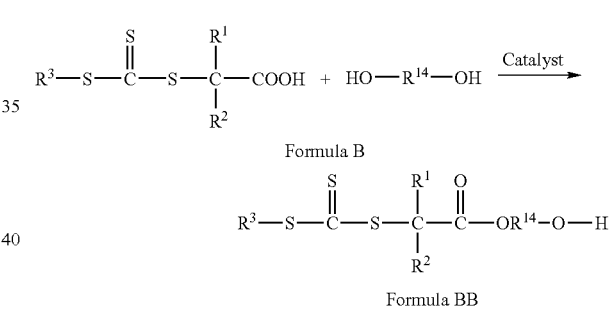

where $R^1$, $R^2$, $R^3$, and $R^{14}$ are defined as hereinabove. In order to form a hydroxyl terminated compound as set forth in Formula BB, the equivalent ratio of hydroxyl groups to carboxylic acid end groups, i.e. OH/COOH is preferably about 2 or greater. If lower equivalent ratios are utilized, non-hydroxyl terminated compounds can exist.

The general reaction for preparing a dithiocarbamate polyol of Formula C where j is 1 is as follows:

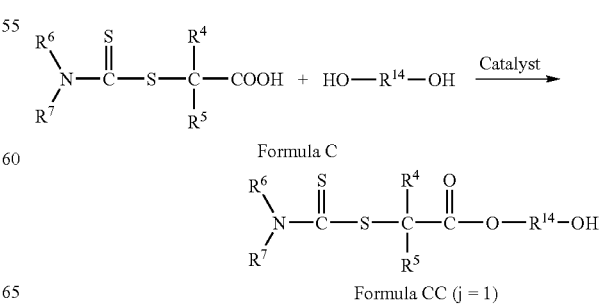

where $R^4$, $R^5$, $R^{14}$, and $R^6$ and $R^7$ are defined herein above. In order to form a hydroxyl terminated compound as set forth in Formula CC, the equivalent ratio of hydroxyl groups to carboxylic acid end groups, i.e. OH/COOH is preferably about 2 or greater. If lower equivalent ratios are utilized, non-hydroxyl terminated compounds can exist.

Reaction of the above dithiocarbamate C compound wherein j is 2 is as follows:

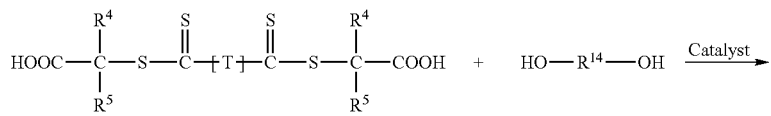

Formula C

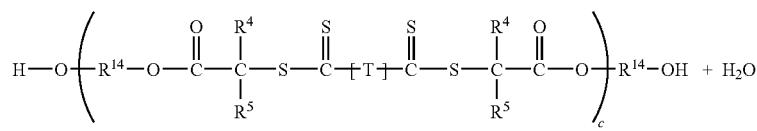

Formula CC (j = 2)

where $R^4$, $R^5$, $R^{14}$, and T are as defined herein above and "c" is from about 1 to about 10 or about 20 and desirably from about 1 to about 5. The number of repeat groups "c" will vary depending upon the equivalent ratio of hydroxyl groups to carboxylic acid groups. Thus, when the OH/COOH ratio is preferably about 2 or greater, generally about one "c" unit will predominate, and the product can be a mixture of different "c" numbers.

When the dithiocarbonate is an alkoxy dithiocarbonate of Formula E, j can be 1 or 2. Where j=1, the general reaction is as follows:

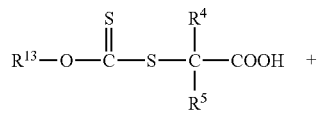

Formula E

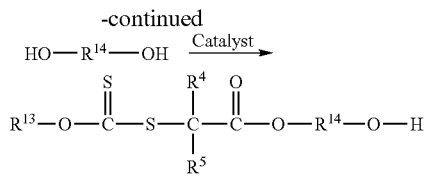

Formula EE (j = 1)

wherein $R^4$, $R^5$, and $R^{13}$ are defined hereinabove. In order to form a hydroxyl terminated compound as set forth in Formula EE, the equivalent ratio of hydroxyl groups to carboxylic acid end groups, i.e. OH/COOH is preferably about 2 or greater. If lower equivalent ratios are utilized, non-hydroxyl terminated compounds can exist.

When the dithiocarbonate is an alkoxy dithiocarbonate of Formula E wherein j=2, the general reaction is as follows

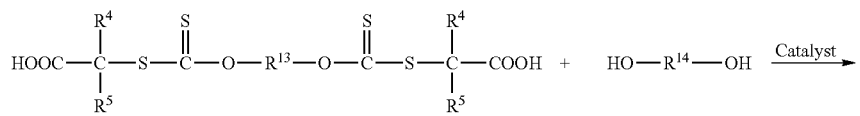

Formula E (where j = 2)

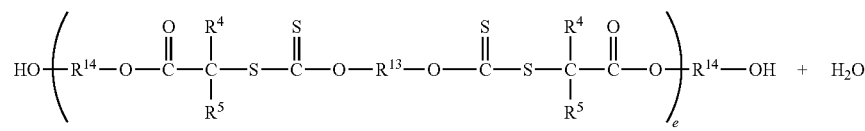

Formula EE (where j = 2)

where $R^4$, $R^5$, and $R^{13}$, are defined herein above and "e" is from about 1 to about 10 or about 20, and desirably from 1 to about 5. The number of repeat groups "e" will vary depending upon the equivalent ratio of hydroxyl groups to carboxylic acid groups. Thus, when the OH—COOH ratio is preferably about 2 or greater, generally about one "e" unit will predominate, and the product can be a mixture of different "e" numbers.

In a similar manner, the reaction of other thiocarbonate compounds and other polyols will form hydroxyl terminated thiocarbonate polymers.

Monomer Incorporation

In a further embodiment, the thiocarbonate compounds and/or the hydroxyl terminated thiocarbonate compounds are reacted with one or more, same or different monomers through a reversible polymerization process, such as a reversible addition—fragmentation transfer (RAFT) polymerization, thereby incorporating the monomer(s) into the backbone of the thiocarbonate compound thus forming a thiocarbonate polymer or copolymer. Although the one or more monomers can first be reacted into the thiocarbonate compounds, it is preferred that the thiocarbonate compounds are reacted to contain hydroxyl end groups before the one or more monomers are reacted into the backbone of the thiocarbonate.

The monomers include one or more conjugated diene monomers or one or more vinyl containing monomers, or combinations thereof. The various one or more free radically polymerizable monomer as well as the various reaction conditions thereof including types of initiators, catalysts, solvents, and the like are set forth in U.S. Patent Nos. U.S. Pat. No. 6,596,889 granted Jul. 22, 2003; U.S. application Ser. No. 10/219,403 filed Aug. 15, 2002; U.S. application Ser. No. 10/278,335 filed Oct. 23, 2002; and U.S. application Ser. No. 10/681,679 filed Oct. 8, 2003, all of which are hereby fully incorporated by reference with regard to all aspects thereof.

The diene monomers have a total of from 4 to about 12 carbon atoms and examples include, but are not limited to, 1,3-butadine, isoprene, 1,3-pentadiene, 2,3-dimethyl-1-3-butadeine, 2-methyl-1,3-pentadiene, 2,3-dimethyl-1,3-pentadiene, 2-phenyl-1,3-butadiene, and 4,5-diethyl-1,3-octadiene, and combinations thereof.

The vinyl containing monomers have the following structure:

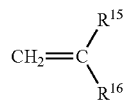

where $R^{15}$ comprises hydrogen, halogen, $C_1$ to $C_4$ alkyl, or substituted $C_1$-$C_4$ alkyl wherein the substituents, independently, comprise one or more hydroxy, alkoxy, aryloxy ($OR^{17}$), carboxy, metal carboxylate (COOM) with M being sodium, potassium, calcium, zinc or the like or an ammonium salt, acyloxy, aroyloxy($O_2CR^{17}$), alkoxy-carbonyl($CO_2R^{17}$), or aryloxy-carbonyl; and $R^{16}$ comprises hydrogen, $R^{17}$, $CO_2H$, $CO_2R^{17}$, $COR^{17}$, CN, $CONH_2$, $CONHR^{17}$, $O_2CR^{17}$, $OR^{17}$, or halogen. $R^{17}$, independently, comprises $C_1$-$C_{18}$ alkyl, substituted $C_1$-$C_{18}$ alkyl, $C_2$-$C_{18}$ alkenyl, aryl, heterocyclyl, aralkyl, or alkaryl, wherein the substituents independently comprise one or more epoxy, hydroxy, alkoxy, acyl, acyloxy, carboxy (and salts), sulfonic acid (and salts), alkoxy- or aryloxy-carbonyl, dicyanato, cyano, silyl, halo and dialkylamino. Optionally, the monomers comprise maleic anhydride, N-vinyl pyrrolidone, N-alkylmaleimide, N-arylmaleimide, dialkyl fumarate and cyclo-polymerizable monomers. Monomers $CH_2=CR^{15}R^{16}$ as used herein include $C_1$-$C_8$ acrylates and methacrylates, acrylate and methacrylate esters, acrylic and methacrylic acid, styrene, a methyl styrene, $C_1$-$C_{12}$ alkyl styrenes with substitute groups both either on the chain or on the ring, acrylamide, methacrylamide, N- and N,N-alkylacrylamide and methacrylonitrile, mixtures of these monomers, and mixtures of these monomers with other monomers. As one skilled in the art would recognize, the choice of comonomers is determined by their steric and electronic properties. The factors which determine copolymerizability of various monomers are well documented in the art. For example, see: Greenley, R. Z., in *Polymer Handbook*, $3^{rd}$ Edition (Brandup, J., and Immergut, E. H. Eds.) Wiley: New York, 1989 pll-53.

Specific monomers or comonomers include the following:

methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates such as glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, and triethyleneglycol methacrylate, itaconic anhydride, itaconic acid; metal salts such as but not limited to sodium and zinc of all monomeric acids, such as but not limited to, itaconic acid and 2-acrylamido-2-methyl-1-propanesulfonic acid, or the like; N-vinylimidazole, vinylpyridine N-oxide, 4-vinylpyridine carboxymethylbetaine, diallyl dimethylammonium chloride, p-styrenesulfonic acid, p-styrenecarboxylic acid, 2-dimethylaminioethyl acrylate and its alkyl/hydrogen halide salts, 2-dimethyl-aminoethyl methacrylate and its alkyl/hydrogen halide salts, N-(3-dimethylaminopropyl) acrylamide, N-(3-dimethylaminoproyl) methacrylamide, diacetone acrylamide, 2-(acetoacetoxy)ethyl methacrylate, 2-(acryloyloxy)ethyl acetoacetate, 3-trialkoxysilylpropylmethacrylate (methoxy, ethoxy, isopropoxy, etc), glycidyl acrylate, 2-hydroxyethyl acrylate, hydroxypropyl acrylate (all isomers), hydroxybutyl acrylate (all isomers), N,N-diethylaminoethyl acrylate, triethyleneglycol acrylate, methacrylamide, N-methylacrylamide, N,N-dimethyl-acrylamide, N-tertbutylmethacrylamide, N,N-butylmethacrylamide, N-methylol-methacrylamide, N-ethylolmethacrylamide, N-tertbutylacrylamide, N,N-butyl-acrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxy-methylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxy silylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxy-methylsilylpropyl acrylate, diisopropoxymethylsilylpropyl acrylate, dimethoxy-silylpropyl acrylate, diethoxysilylpropyl acrylate, dibutoxysilylpropyl acrylate, diisopropoxysilylpropyl amiate, vinyl acetate, vinyl butyrate, vinyl benzoate, vinyl chloride, vinyl fluoride, vinyl bromide, maleic anhydride, N-phenylmaleimide, N-butylmaleimide, N-vinylpyrrolidone, N-vinylcarbazole, butadiene, isoprene, chloroprene, ethylene, and propylene, and combinations thereof.

Preferred monomers are $C_1$-$C_{18}$ acrylates; acrylic acid; $C_1$-$C_8$ monoalkyl and dialkyl acrylamides; a combination of $C_1$-$C_8$ acrylates and methacrylates; a combination of said acrylamides and $C_1$-$C_8$ monoalkyl and dialkyl methacrylamides; styrene; butadiene; isoprene and acrylonitrile.

In order to initiate the free radical polymerization process, it is often desirable to utilize an initiator as a source for initiating free radicals. Generally, the source of initiating radicals can be any suitable method of generating free radicals such as the thermally induced homolytic scission of a suitable compound(s) (thermal initiators such as peroxides, peroxyesters, or azo compounds), the spontaneous generation from monomer (e.g., styrene), redox initiating systems, photochemical initiating systems or high energy radiation such as electron beam, X- or gamma-radiation. The initiating system is chosen such that under the reaction conditions there is no substantial adverse interaction of the initiator or the initiating radicals with the transfer agent under the conditions of the experiment. The initiator should also have the requisite solubility in the reaction medium or monomer mixture. The thiocarbonate compounds of the invention can serve as an initiator, but the reaction must be run at a higher temperature. Therefore, optionally it is desirable to utilize an initiator other than the thiocarbonates compounds of the present invention.

Thermal initiators are chosen to have an appropriate half-life at the temperature of polymerization. These initiators can include one or more of the following compounds: 2,2'-azobis(isobutyronitrile)(AIBN), 2,2'-azobis(2-cyano-2-butane), dimethyl 2,2'-azobisdimethylisobutyrate, 4,4'-azobis(4-cyanopentanoic acid), 1,1'-azobis (cyclohexanecarbanitrile), 2-(t-butylazo)-2-cyanopropane, 2,2'-azobis [2-methyl-N-(1,1)-bis(hydoxymethyl)-2-hydroxyethyl] propionamide, 2,2'-azobis[2-methyl-N-hydroxyethyl)]-propionamide, 2,2'-azobis(N,N'-dimethyleneisobutyramidine) dihydrochloride, 2,2'-azobis(2-amidinopropane) dihydrochloride, 2,2'-azobis(N,N'-dimethyleneisobutyramine), 2,2'-azobis (2-methyl-N-[1,1-bis(hydroxymethyl)-2-hydroxyethyl] propionamide), 2,2'-azobis(2-methyl-N-[1,1-bis(hydroxymethyl) ethyl] propionamide), 2,2'-azobis[2-methyl-N-(2-hydroxyethyl) propionamide], 2,2'-azobis(isobutyramide) dehydrate, 2,2'-azobis(2,2,4-trimethylpentane), 2,2'-azobis(2-methylpropane), t-butyl peroxyacetate, t-butyl peroxybenzoate, t-butyl peroxyoctoate, t-butylperoxy-neodecanoate, t-butylperoxy isobutyrate, t-amyl peroxypivalate, t-butyl peroxypivalate, diisopropyl peroxydicarbonate, dicyclohexyl peroxydicarbonate, dicumyl peroxide, dibenzoyl peroxide, dilauroylperoxide, potassium peroxy-disulfate, ammonium peroxydisulfate, di-t-butyl hyponitrite, dicumyl hyponitrite.

Photochemical initiator systems are chosen to have the requisite solubility in the reaction medium or monomer mixture and have an appropriate quantum yield for radical production under the conditions of the polymerization. Examples include benzoin derivatives, benzophenone, acyl phosphine oxides, and photo-redox systems production under the conditions of the polymerization; these initiating systems can include combinations of the following oxidants and reductants:

oxidants: potassium peroxydisulfate, hydrogen peroxide, t-butyl hydroperoxide reductants: iron (11), titanium (111), potassium thiosulfite, potassium bisulfite.

Other suitable initiating systems are described in recent texts. See, for example, Moad and Solomon "The Chemistry of Free Radical Polymerization". Pergamon, London. 1995. pp 53-95.

The preferred initiators of the present invention are 2,2'-azobis (isobutyronitrile)(AIBN), or 4,4'-azobis(4-cyanopentanoic acid), or 2,2'-azobis (2-cyano-2-butane), or 1,1'-azobis (cyclohexanecarbanitrile). The amount of initiators utilized in the polymerization process can vary widely as generally from about 0.001 percent to about 99 percent, and desirably from about 0.01 percent to about 50 or 75 percent based on the total moles of chain transfer agent utilized. Preferably small amounts are utilized from about 0.1 percent to about 5, 10, 15, 20, or 25 mole percent based on the total moles of chain transfer agent utilized, i.e. said s,s'-bis-($\alpha,\alpha'$-disubstituted-$\alpha''$-acetic acid)-trithiocarbonates compounds. In order to form polymers which are predominately telechelic, initiators other than the above thiocarbonate compounds are utilized in lesser amounts, such as from about 0.001 percent to about 5 percent, desirably from about 0.01 percent to about 4.5 percent, and preferably from about 0.1 percent to about 3 percent based on the molar equivalent to the total moles of chain transfer agent utilized.

Optionally, as noted above, solvents can be utilized in the free radical polymerization process. Examples of such solvents include, but are not limited to, $C_6$-$C_{12}$ alkanes, ethyl acetate, toluene, chlorobenzene, acetone, t-butyl alcohol, n-methylpyrrolidone, dimethylformamide, and super critical $CO_2$. The solvents are chosen so that they do not substantially chain transfer themselves. The amount of solvent utilized in the present invention polymerization process is generally from about 10 percent to about 500 percent the weight of the monomer, and preferably from about 50 percent to about 200 percent the weight of the monomer utilized in the polymerization.

The one or more conjugated diene and/or vinyl monomers can be incorporated into the backbone of the thiocarbonate compound before it is reacted with a polyol and the same reaction scheme is set forth in U.S. Pat. No. 6,596,899 granted Jul. 22, 2003, or in U.S. patent application Ser. No. 10/278,335 filed Oct. 23, 2002, or in U.S. patent application Ser. No. 10/681,679 filed Oct. 8, 2003 which are hereby fully incorporated by reference.

Alternatively, desirably, and in a similar manner, the various one or more conjugated diene monomers and/or the one or more vinyl monomers are incorporated into the backbone of the hydroxyl-terminated thiocarbonate compound.

With respect to the hydroxyl terminated thiocarbonate of Formula AA, the general reaction scheme for reacting one or more conjugated diene monomers and/or one or more vinyl monomers into the backbone of the hydroxyl-terminated trithiocarbonate compound is as follows:

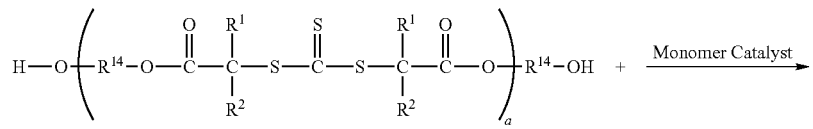

Formula AA

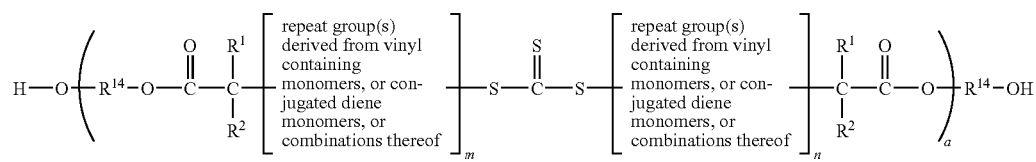

Block Formula AA or

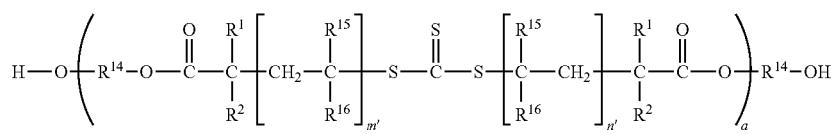

Block Formula AA' wherein $R^1$, $R^2$, $R^{14}$, $R^{15}$, and $R^{16}$ are defined hereinabove, "a" is as set forth hereinabove, and m, m', n and n', independently, is generally from about 1 to about 10,000, desirably from about 2 to about 500, and preferably from about 5 to about 100. Naturally, any remaining monomer is removed.

With respect to the hydroxyl-terminated trithiocarbonate compound of Formula BB, the general reaction scheme is as follows:

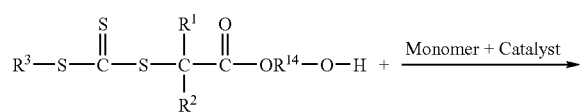

Formula BB

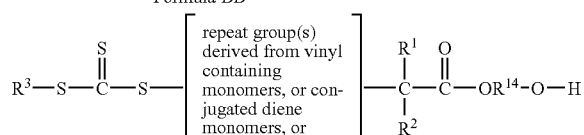

Block Formula BB or

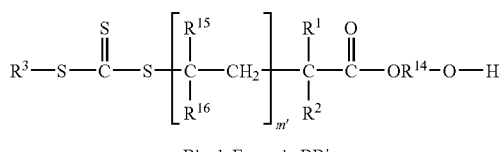

Block Formula BB' wherein $R^1$, $R^2$, $R^3$, $R^{14}$, $R^{15}$, and $R^{16}$ are defined hereinabove, and m and m', independently, is generally from about 1 to about 10,000, desirably from about 2 to about 500, and preferably from about 5 to about 100. Naturally, any remaining monomer is removed.

With regard to the hydroxyl-terminated trithiocarbonate compound of Formula CC where j is 1, the general reaction scheme is as follows:

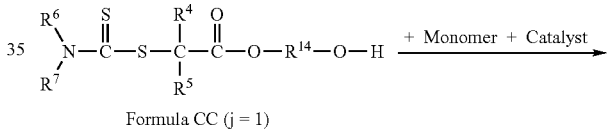

Formula CC (j = 1)

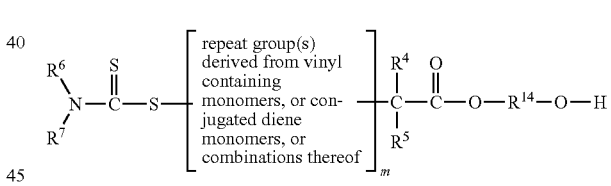

Block Formula CC (j = 1)

or

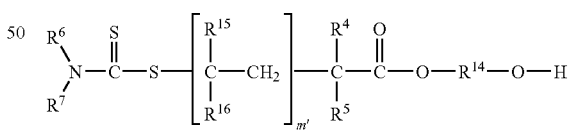

Block Formula CC' wherein $R^4$, $R^5$, $R^6$, $R^7$, $R^{14}$, $R^{15}$, and $R^{16}$ are defined hereinabove, and m and m' is generally from about 1 to about 10,000, desirably from about 2 to about 500, and preferably from about 5 to about 100. Naturally, any remaining monomer is removed.

With respect to the high temperature dithiocarbonate compound of Formula CC where j is 2, the general reaction scheme is as follows.

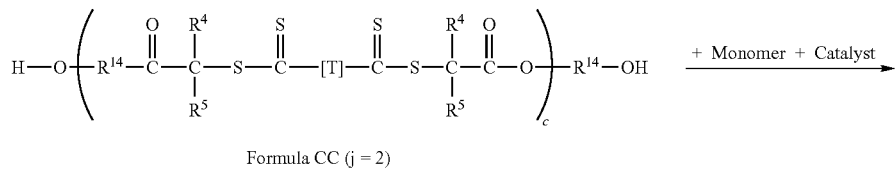

Formula CC (j = 2)

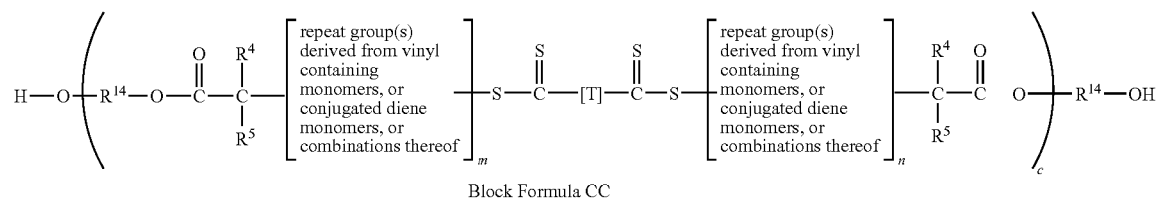

Block Formula CC or

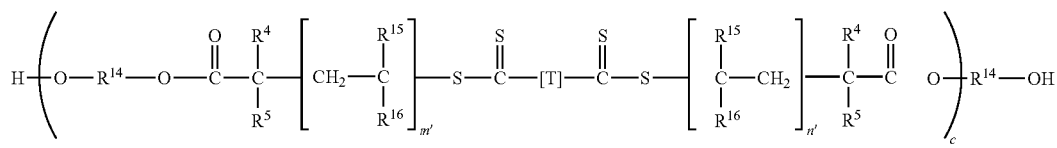

Block Formula CC' wherein $R^4$, $R^5$, $R^{14}$, $R^{15}$, $R^{16}$, and T are defined hereinabove, wherein c is from about 1 to about 10 or about 20, and preferably from 1 to about 5, and wherein m, m', n, and n', independently, are generally from about 1 to about 10,000, desirably from about 2 to about 500, and preferably from about 5 to about 100. Naturally, any remaining monomer is removed.

With respect to the high temperature dithiocarbonate of Formula EE, the general reaction scheme is as follows:

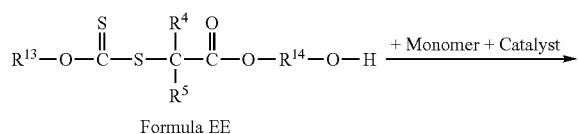

Formula EE

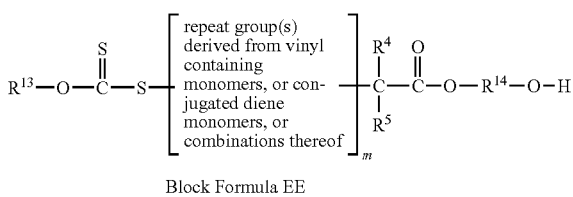

Block Formula EE or

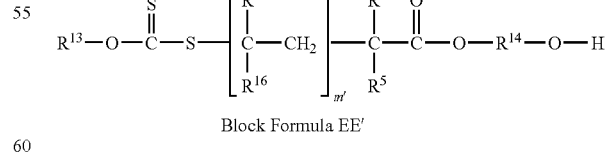

Block Formula EE' wherein $R^4$, $R^5$, $R^{13}$, $R^{14}$, $R^{15}$, and $R^{16}$, are defined hereinabove, wherein m and m' is generally from about 1 to about 10,000, desirably from about 2 to about 500, and preferably from about 5 to about 100. Naturally any remaining monomer is removed.

With respect to the hydroxyl-terminated dithiocarbonate of Formula EE where j is 2, the general reaction scheme is as follows:

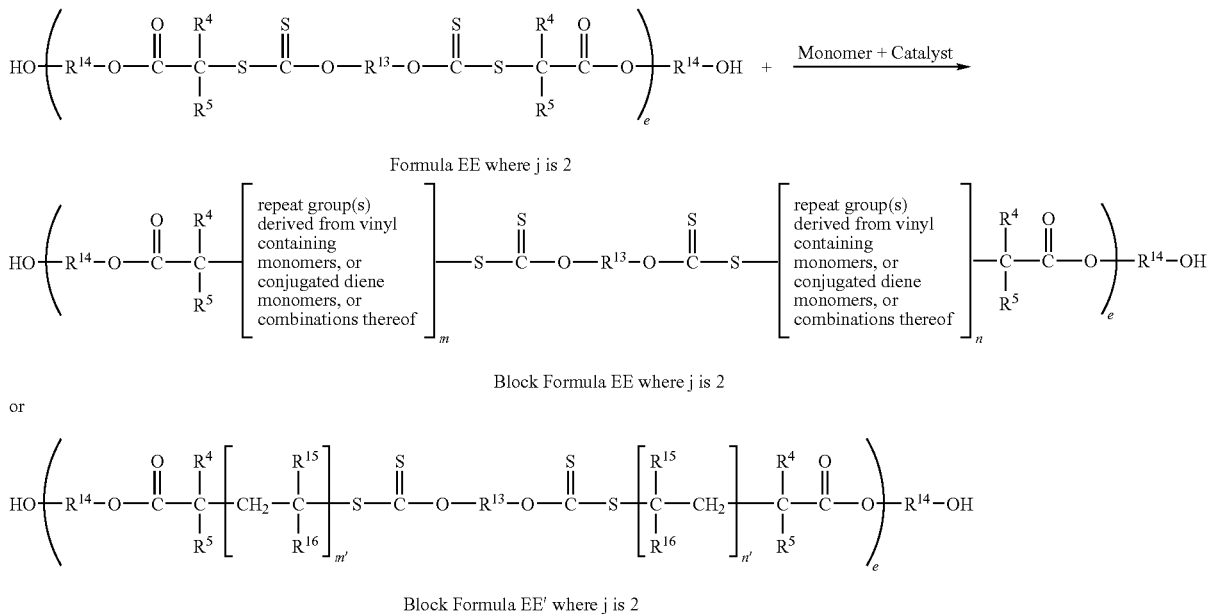

Formula EE where j is 2

Block Formula EE where j is 2 or

Block Formula EE' where j is 2 wherein $R^4$, $R^5$, $R^{13}$, $R^{14}$, $R^{15}$, and $R^{16}$, are defined hereinabove, wherein e is from about 1 to about 10 or about 20, and preferably from about 1 to about 5, and wherein m, m', n, and n', independently, is from about 1 to about 10,000, desirably from about 2 to about 500, and preferably from about 5 to about 100. Naturally any remaining monomer is removed.

Reactions of other thiocarbonates with various conjugated diene and/or vinyl monomers react in a similar manner, and reaction mechanisms are set forth in more detail in U.S. Pat. No. 6,596,899 issued Jul. 22, 2003; U.S. patent application Ser. Nos. 10/219,403 filed Aug. 15, 2002; Ser. No. 10/278,335 filed Oct. 23, 2002; and Ser. No. 10/681,679 filed Oct. 8, 2003 which are hereby fully incorporated by reference.

The resulting polymers or copolymers are either telechelic polymers with hydroxyl functional groups at both ends of the chain, or a polymer having a single hydroxyl functional end group and also a small amount of an initiator terminated chain (formed by using a conventional initiator such as AIBN). As stated above, the ratios between the resulting polymers can be controlled to give desired results and generally depend on the amount of initiator utilized. The greater the amount of the other initiator utilized proportionally decreases the amount of telechelic polymers formed. Generally, the number of the repeat groups of the one or more monomers per polymer chain such as m, m', n or n' have a wide range as set forth above. Inasmuch as one or more vinyl monomers and/or one or more diene monomers can be utilized, it is to be understood that repeat groups of the hydroxyl terminated thiocarbonate polymers or copolymers of the present invention can be the same or different. That is, random copolymers, terpolymers, etc., can be formed within the one or more m, m', n, or n' blocks as noted, as well as block copolymers can be formed by initially adding one monomer and then subsequently adding a different monomer (e.g. an internal block copolymer).

The invention has wide applicability in the field of free radical polymerization and can be used to produce polymers and compositions for coatings, a wide variety of which can be applied to numerous different substrates. Such coatings can further include pigments, durability agents, corrosion and oxidation inhibitors, rheology control agents, metallic flakes and other additives. Block and star, and branched polymers can be used as compatibilizers, thermoplastic elastomers, dispersing agents or rheology control agents. Additional applications for polymers of the invention are in the fields of imaging, electronics (e.g., photoresists), engineering plastics, adhesives, sealants, and polymers in general.

The reaction conditions are chosen as known to one skilled in the art so that the temperature utilized will generate a radical in a controlled fashion, wherein the temperature is generally from about room temperature to about 200° C. The reaction can be run at temperatures lower than room temperature, but it is impractical to do so. The temperature often depends on the initiator chosen for the reaction, for example, when AIBN is utilized, the temperature generally is from about 40° C. to about 80° C., when 4,4'-azobis(4-cyanovaleric) acid is utilized, the temperature generally is from about 50° C. to about 90° C., when di-t-butylperoxide is utilized, the temperature generally is from about 110° C. to about 160° C., when a thiocarbonate is utilized, the temperature is generally from about 80° C. to about 200° C.

EXAMPLE 1

Synthesis of the Monohydroxyl Terminated Dithiocarbamate Compound

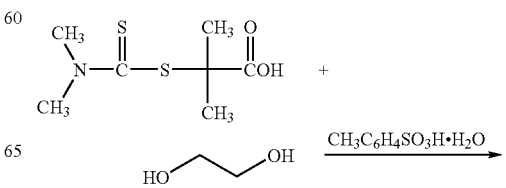

-continued

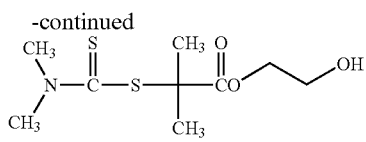

Procedure:

In a 1000 ml jacketed reaction vessel equipped with a mechanical stirrer, a thermometer, a reflux condenser, distillation adaptor, and an addition funnel, 500 grams of ethylene glycol was added and heated to 90° C. under nitrogen. A mixture of 200 grams of the dithiocarbonate and 18.37 grams of the p-toluenesulfonic acid monohydrate was added through the addition funnel dropwise to maintain reaction temperature. A mixture of dithiocarbonate and p-toluenesulfonic acid was added, heated to 110° C. and 60 mmHg of partial vacuum was pulled to collect water. When no more water was collected and the head temperature dropped and levels dropped off, the vacuum was slowly increased to full vacuum to distill off excess ethylene glycol. When reaction temperature exceeded 90° C., the reaction was stopped. For purification, 250 ml toluene was added when the reaction had cooled and stirred to room temperature. The mixture was then transferred to a separatory funnel and extracted three times with 100 ml saturated sodium carbonate. The aqueous fractions were discarded and the organic (toluene) fraction collected. 10 grams of magnesium sulfate was added. After one hour, the filter contents were concentrated with a rotavaporator at 80° C., full vacuum, for an hour. An orange, viscous product was collected and the structure confirmed with mass spectrometry, nuclear magnetic resonance and hydroxyl number.

EXAMPLE 2

Synthesis of Dihydroxyl Dithiocarbamate Compound

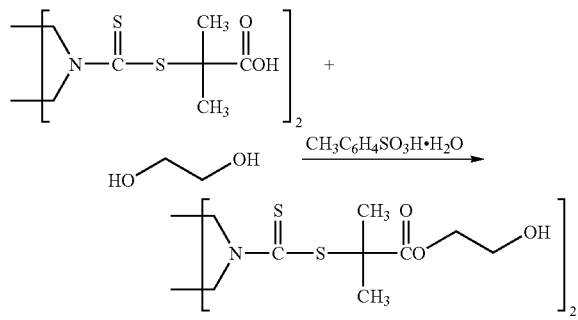

Procedure:

In a 500 ml jacketed reaction vessel equipped with a mechanical stirrer, a thermometer, a reflex condenser, distillation adaptor, and an addition funnel, 150 grams of ethylene glycol and 5.57 grams of the p-toluenesulfonic acid monohydrate was added and heated to 110° C. under nitrogen. A mixture of 60 grams of the dithiocarbonate was added through the addition funnel dropwise to maintain reaction temperature. Once added, the partial vacuum was increased to 60 mmHg to remove water. When little water was coming off and head temperature dropped and levels dropped off, the temperature was increased to 120° C. to remove more water. When no more water was removed and head temperature dropped and stabilized, the vacuum was increased to full vacuum to remove excess ethylene glycol. When temperature exceeded 110° C., the heat was turned off. When reaction was room temperature, added 65 ml methyl isobutyl ketone and stirred till homogenous. Added 33 ml of 5% sodium hydroxide, stirred and transferred to a separatory funnel. Collected organic (methyl isobutyl ketone) fraction. Extracted aqueous layer two times each with 16 ml methyl isobutyl ketone. Added these two methyl isobutyl ketone fractions to the previous organic fraction. The organic fraction was stirred at room temperature until a white precipitate dropped out and became thick. Refrigerated, buchner filtered and collected white solid. Confirmed structure by nuclear magnetic resonance, mass spectrometry and hydroxyl number.

EXAMPLE 3

Synthesis of Monohydroxyl Dithiocarbamate Polymer Containing Repeat Units Derived from Ethyl Acrylate

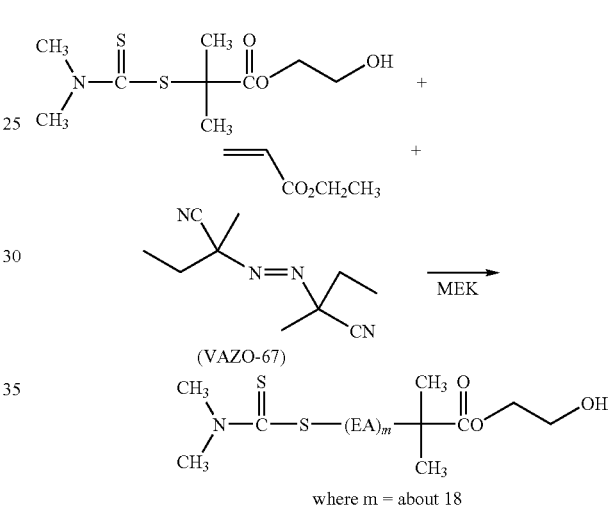

where m = about 18

Procedure:

In a 1000 ml reaction vessel equipped with mechanical stirrer, thermometer, reflux condenser and nitrogen purge, 44.2 grams of the monohydroxyl terminated dithiocarbonate, 395.9 grams of ethyl acrylate, 400 ml of MEK, and 0.5071 grams of Azo catalyst were added. After a nitrogen blanket was applied, the reactants were heated to 65° C. After no further exotherm was observed, the reactants were heated to 80° C. for a period of about 5 hours. The solvent was removed by rotavaporation under full vacuum and 80° C. and a viscous product collected. The structure was confirmed by size exclusion chromatography, hydroxyl number and matrix-assisted laser desorbtion ionization.

EXAMPLE 4

Synthesis of Dihydroxyl Dithiocarbamate Polymer Containing Repeat Units Derived from Butyl Acrylate

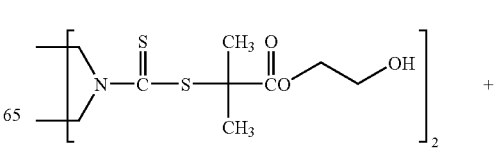

-continued

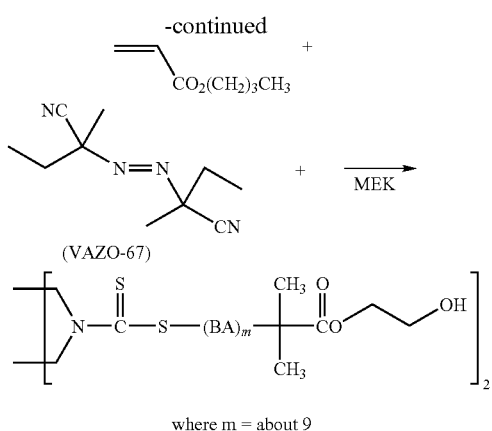

(VAZO-67)

where m = about 9

Procedure:

In a 2000 ml reaction vessel equipped with mechanical stirrer, thermometer, reflux condenser and nitrogen purge, 58.0 grams of the dihydroxyl terminated dithiocarbonate, 524.33 grams of butyl acrylate, 0.3323 grams of Azo catalyst, and 580 ml of MEK were added. After a nitrogen blanket was applied, the reactants were heated to 65° C. for a period of about 4.5 hours. Solvent was removed by rotavaporation under full vacuum and 80° C. The viscous product was collected. Confirmed structure by size exclusion chromatography, hydroxyl number and matrix-assisted laser de desorbtion ionization.

EXAMPLE 5

Synthesis of a Dihydroxyl Dithiocarbamate Copolymer Containing Repeat Units Derived from Ethyl Acrylate and Acrylonitrile

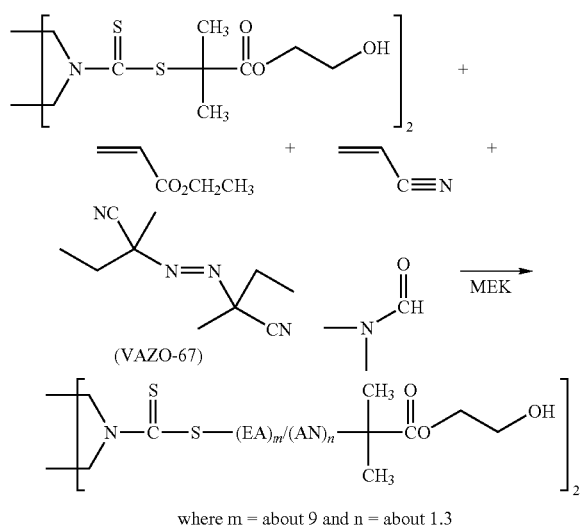

where m = about 9 and n = about 1.3

Procedure:

In a 2000 ml reaction vessel equipped with mechanical stirrer, thermometer, reflux condenser and nitrogen purge, 124.5 grams of the monohydroxyl terminated dithiocarbonate, 465 grams of ethyl acrylate, 35 grams of acrylonitrile, 0.9611 grams of Azo catalyst, and 625 ml of dimethylforamide were added. After a nitrogen blanket was applied, the reactants were heated to 65° C. for a period of about 8.5 hours. Solvent was removed by rotavaporation under full vacuum and 80° C. The viscous product was collected. Confirmed structure by size exclusion chromatography, hydroxyl number and matrix-assisted laser desorbtion ionization.

EXAMPLE 6

Synthesis of a Dihydroxyl Dithiocarbamate Copolymer Containing Repeat Units Derived from Ethyl Acrylate and Diacetone Acrylamide

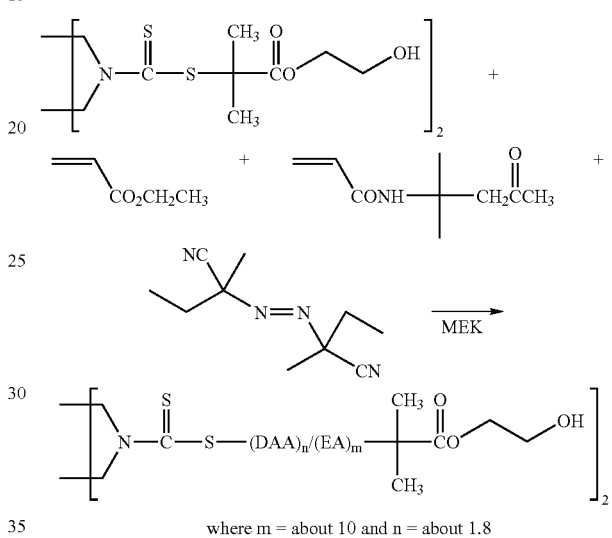

where m = about 10 and n = about 1.8

Procedure:

In a 2000 ml reaction vessel equipped with mechanical stirrer, thermometer, reflux condenser and nitrogen purge, 139.324 grams of the dihydroxyl terminated dithiocarbonate, 560 grams of ethyl acrylate, 140 grams of diacetone acrylamide, 840 ml of MEK, and 0.8073 grams of Azo catalyst were added. After a nitrogen blanket was applied, the reactants were heated to 65° C. After no further exotherm was observed, the reactants were heated to 80° C. for a period of about 7 hours. Removed solvent by rotavaporation under full vacuum and 80° C. The viscous product was collected. Confirmed structure by size exclusion chromatography, hydroxyl number and matrix-assisted laser desorbtion ionization.

EXAMPLE 7

Synthesis of the Mono-Dihydroxyl Terminated Dithiocarbamate Compound (from Mono Dithiocarbonate and Trimethylolpropane).

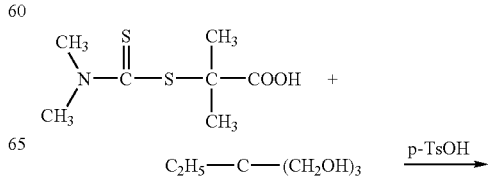

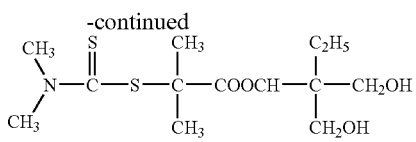

Procedure:

In a 100 ml jacketed reaction vessel equipped with a mechanical stirrer, a thermometer, a reflex condenser, distillation adaptor, and an additional funnel, 33 grams of trmethyloylpropane was added and heated to 80° C. under nitrogen. A mixture of 10 grams of the dithiocarbonate and 0.87 grams of the p-toluenesulfonic acid monohydrate was added through the addition funnel in aliquots to maintain reaction temperature. Once the mixture of dithiocarbonate and p-toluenesulfonic acid was added, it was heated to 110° C. and 60 mmHg of partial vacuum to collect water. The reaction was stopped when no more water was collected and the reaction head temperature had dropped. For purification, 50 ml toluene was added and stirred at approximately 70° C., cooled and collected top toluene layer, concentrate. An orange, viscous product was collected and the structure was confirmed with mass spectrometry, nuclear magnetic resonance and hydroxyl number.

EXAMPLE 8

Synthesis of Dihydroxyl Dithiocarbamate Compound (1,3 Propanediol Derivative)

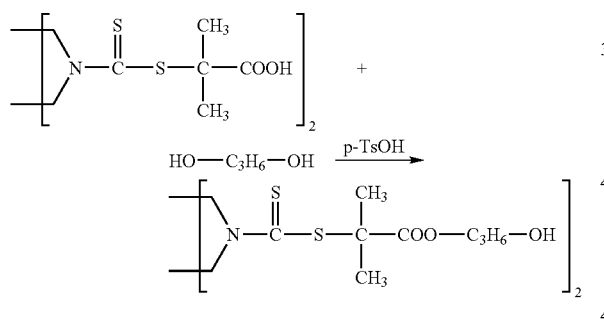

Procedure:

In a 2000 ml jacketed reaction vessel equipped with a mechanical stirrer, a thermometer, a reflex condenser, distillation adaptor, and an addition funnel, 685 grams of 1,3 propanediol and 26.1 grams of the p-toluenesulfonic acid monohydrate was added and heated to 110° C. under nitrogen. Dithiocarbonate was added in four aliquots over one hour. Once added, distillation apparatus was attached and the partial vacuum was increased to 60 mmHg to remove water. When little water was coming off and the head temperature had dropped and leveled off, the temperature was increased to 120° C. to remove more water. When no more water was removed and the head temperature had stabilized, the vacuum was increased to full to remove excess 1,3 propanediol. When the temperature exceeded 100° C., the heat was turned off. When reaction reached room temperature, 400 ml chloroform was added and stirred till homogenous and then transferred to a separatory funnel and washed three times with 200 ml saturated sodium carbonate solution. The chloroform layer was collected, 10 g magnesium sulfate was added and let sit for at least an hour. The chloroform fraction was filtered and concentrated. To the concentrate was added 400 ml toluene and stirred at 80° C. till homogenous. Then it was stirred to room temperature. Refrigerated, buchner filter and collected light yellow solid. Confirmed structure by nuclear magnetic resonance, mass spectrometry and hydroxyl number.

EXAMPLE 9

Synthesis of a Dihydroxy Trithiocarbonate Compound of Formula AA

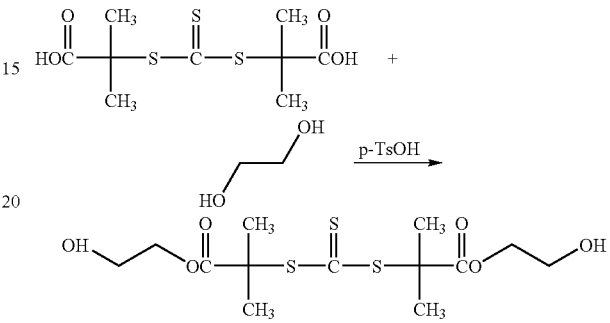

Procedure:

The reaction was run in a 100 ml, 3 port reaction vessel equipped with a magnetic stirring, mantle, thermowatch, condenser, distillation adaptor, receiver, thermometers, partial vacuum, solid addition funnel, under a nitrogen blanket. 50 grams of ethylene glycol was then charged under a nitrogen blanket and the solution heated to 80° C. At 80° C., 20 grams of TTC and 2.7 grams of pTSA were slowly added through addition funnel in aliquots. When the TTC/pTSA was added, the partial vacuum was started and increased to 60 mmHg. When no more condensate was collected at 110° C., 60 mmHg, the temperature was set to 90° C. The vacuum was increased to full to distill off diol. When pot temperature was 90° C. to 95° C., the heat was turned off and workup. Confirmed structure by nuclear magnetic resonance, mass spectrometry and hydroxyl number.

EXAMPLE 10

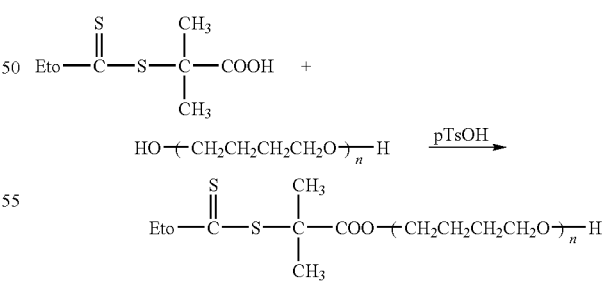

Procedure:

O-ethyl-s-(isobutyric acid) xanthate (100 g), 300 g of polytetrahydrofuran, (molecular number equals about 250) and p-toluenesulfonic acid (10 g) were mixed and heated to 110° C. to distill off water that is formed. After five hours, unreacted polytetrahydrofuran was distilled under 1 mmHg vacuum. The residue was dissolved in 500 ml ether, dried over sodium sulfate and concentrated to yield oil. Confirmed structure by nuclear magnetic resonance, mass spectrometry and hydroxyl number.

Thermoplastic Polyurethanes (TPU) Made from Hydroxyl-Terminated Thiocarbonate Compounds, Polymers, and Copolymers.

Thermoplastic polyurethanes are generally formed in one embodiment of the invention by reacting the hydroxyl group terminated thiocarbonate compounds, polymers, or copolymers, or a combination thereof with an isocyanate group-containing compound optionally in the presence of a catalyst generally followed by chain extension. The thermoplastic urethanes can be made by can be made preferably by a waterborne process, or by a solvent process, or by extrusion. Optionally thermosets can be formed utilizing either crosslinking agents or self-crosslinking compounds incorporated within various urethane components. The term "polyurethane composition" when utilized in the specification generally refers to a composition containing reagents utilized to form a polyurethane, or a composition subsequent to the reaction of the polyurethane forming reagents by some process or mechanism. The thermoplastic polyurethanes of the invention are able to be melted and reshaped by some process such as extrusion or molding, or cast into film from solution and are thus substantially uncrosslinked.

Isocyanates

Suitable isocyanates comprise mono-isocyanates and polyisocyanates such as di-isocyanates, tri-isocyanates, and functionalized isocyanates having a total of from 4 to about 10, or about 15, or about 20 carbon atoms, or mixtures thereof. In one embodiment, suitable isocyanates have an average of one or more, or about two to about four isocyanate groups, preferably an average of about two isocyanate groups and include aliphatic, cycloaliphatic, aromatic including any aliphatic groups, and trialkoxysilylalkyl isocyanates, used alone or in mixtures of two or more. Diisocyanates are highly preferred in order to produce thermoplastic polyurethanes.

Specific examples of suitable aliphatic polyisocyanates include alpha, omega-alkylene diisocyanates having from 5 to about 20 carbon atoms, such as tetramethylene diisocyanate, hexamethylene-1,6-diisocyanate (HDI), decamethylene diisocyanate, 1,1,2-dodecane diisocyanate, 2,2,4-trimethyl-hexamethylene diisocyanate, 2,4,4-trimethyl-hexamethylene diisocyanate, 2-methyl-1,5-pentamethylene diisocyanate, and the like. Polyisocyanates having fewer than 5 carbon atoms can be used but are less preferred because of their high volatility and toxicity. Aromatic aliphatic isocyanates can also be used such as 1,2-, 1,3- and 1,4-xylylene diisocyanates and m-tetramethylxylyene diisocyanate (TMXDI). Preferred aliphatic polyisocyanates include hexamethylene-1,6-diisocyanate, 2,2,4-trimethyl-hexamethylene-diisocyanate, and 2,4,4-trimethyl-hexamethylene diisocyanate.

Specific examples of suitable cycloaliphatic polyisocyanates contain from about 6 to about 20 carbon atoms and include cyclobutane-1,3-diisocyanate, 1,2-, 1,3- and 1,4-cyclohexane diisocyanates, 2,4- and 2,6-methylcyclohexane diisocyanate, 4,4'- and 2,4'-dicyclohexyldiisocyanates, 1,3,5-cyclohexane triisocyanates, isocyanatomethylcyclohexane isocyanates, isocyanatoethylcyclohexane isocyanates, bis(isocyanatomethyl)-cyclohexane diisocyanates, 4,4'- and 2,4'-bis(isocyanatomethyl) dicyclohexane, isophorone diisocyanate, and the like including derivatives, dimers, and trimers thereof. Preferred cycloaliphatic polyisocyanates include dicyclohexylmethane diisocyanate and isophorone diisocyanate.

Examples of suitable aromatic polyisocyanates contain from about 8 to about 20 carbon atoms and include 2,4- and 2,6-hexahydrotoluenediisocyanate, 1,2, 1,3, and 1,4-phenylene diisocyanates, triphenyl methane-4,4', 4"-triisocyanate, naphthylene-1,5-diisocyanate, 2,4- and 2,6-toluene diisocyanate (TDI), 2,4'-, 4,4'- and 2,2-biphenyl diisocyanates, 2,2'-, 2,4'- and 4,4'-diphenylmethane diisocyanates (MDI), polyphenyl polymethylene polyisocyanates (PMDI), mixtures of MDI and PMDI, mixtures of PMDI and TDI, and modified polyisocyanates derived from the above isocyanates and polyisocyanates, including dimers and trimers thereof, or combinations thereof.

Examples of suitable trialkoxysilylalkyl isocyanates include trimethoxy-silylpropyl and triethoxysilylpropyl isocyanate.

The mole equivalent ratio of all NCO groups to all OH terminated compounds such as hydroxyl terminated thiocarbonates, the various hydroxyl-terminated compounds such as polyols which are reacted with an isocyanate, the various dispersants, and the like is generally in excess so that chain extension subsequently can be carried out and generally is from about 1.0 or about 1.25 to about 5.0; desirably from about 1.4 to about 2.2 and more desirably from about 1.4 to about 2.0 with respect to waterborne prepolymers and generally lower with respect to solvent borne systems.

Ionic Dispersants, or Nonionic Dispersants, or Combinations Thereof.

Various ionic or nonionic dispersants known to the art and to the literature are generally utilized whenever a dispersion or a waterborne polyurethane is desired. The ionic dispersants can be compounds which contain the following cations:

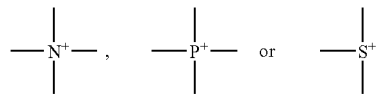

or compounds which contain the following anions: —SO$_3^-$, —OSO$_3^-$, —PO$_2^-$. —PO$_3^-$, —OPO$_3^-$, or preferably —COO$^-$. In addition, it should be recognized that the dispersing groups can be incorporated into the polymer backbone using the thiocarbonate compounds in combination with the previously described vinyl containing monomers that include anionic, cationic, and nonionic functional groups that are well-known to impart water dispersability character to the polyurethane backbone. Examples of such functional groups are carboxyl groups, sulfonic acid groups and the salts thereof. Exemplary vinyl containing monomers that impart water dispersability characteristics to the polyurethane backbone are acrylic and methacrylic acids and the metal or ammonium salts thereof. The dispersing agent formed from the thiocarbonate typically would contain hydroxyl functionality as described herein and can be prepared in a separate synthesis reactor or in the same reactor as the prepolymer (just prior to the urethane synthesis or during urethane synthesis).

When ionic dispersants are utilized, desirably they are subsequently neutralized, that is some and up to all of the ionic dispersants are neutralized with the requirement that a stable dispersion be produced. The amount of the dispersants neutralized will vary depending upon the type of the dispersant, the type of urethane polymer, and the like.

With regard to the various anionic dispersants, e.g. acid dispersants, which are preferred, such compounds generally contain a hydrophilic functional group such as a carboxyl or hydroxyl so that the urethane can be dispersed into water, and may or may not be crosslinkable. A preferred class of anionic dispersants include hydroxy-carboxylic acids having the general formula $(HO)_xQ(COOH)_y$, wherein Q is a straight or branched hydrocarbon radical having 1 to 16 carbon atoms, and x and y are each, independently, 1 to 3, x preferably being 2 and y being 1. Examples of such hydroxy-carboxylic acids include citric acid, dimethylol propanoic acid (DMPA), dimethylol butanoic acid (DMBA), glycolic acid, thioglycolic acid, tartaric acid, dihydroxy tartaric acid, lactic acid, malic acid, dihydroxymalic acid. Dihydroxy-carboxylic acids are preferred with dimethylolpropanoic acid (DMPA) being most preferred. If desired, the carboxyl containing diol or triol may be incorporated into a polyester by reaction with a dicarboxylic acid before being incorporated into the polyurethane prepolymer. The typical amount of such ionic dispersants when utilized can range from about 0.1 to about 50 parts by weight in one aspect, from about 5 to about 30 parts by weight in another aspect and from about 10 to 25 parts by weight in a further aspect, based upon the 100 parts by weight of the formed final polyurethane on a dry weight basis.

When preparing polyurethane dispersions according to the invention the dispersing groups can be derived from ionic polyester polyols, ionic polyethers and polycarbonate polyols. For example, in ionic polyester polyols, the ionic character which these polyols exhibit is based on the condensation of monomers which, in addition to the functional groups required for the condensation (for example hydroxyl, amino and carboxyl groups), contain sulfonic acid, carboxylic acid and/or phosphonic acid groups or sulfonate, carboxylate and/or phosphonate groups. A commercial example of an ionic/ionizable polyol is Lexorez 1405-65 (carboxylic acid functional polyester polyols marketed by Inolex Chemical Company).

Nonionic dispersants include alkylene oxide compounds having repeat groups either in the backbone, or in the side chain (preferred), or combinations thereof. By the term "alkylene oxide" it is meant alkylene oxide and substituted alkylene oxide compounds having from 2 to 10 carbon atoms. Main chain nonionic dispersants generally have at least two repeat groups and desirably at least several repeat groups between the usually hydroxyl-terminated end groups of the oligomer or polymer. A preferred anionic dispersant is polyethylene glycol.

The nonionic dispersants containing poly(alkylene oxide) side chains if used in this invention in an amount to subsequently partially or fully form a waterborne polyurethane; that is from about 0.1 to about 40 parts by weight and preferably about 5 to about 30 parts by weight, based upon the 100 parts by weight of the formed final polyurethane on a dry weight basis. At least about 50 wt. %, preferably at least about 70 wt. %, and more preferably at least about 90 wt. % of the poly(alkylene oxide) side-chain units comprise poly(ethylene oxide), and the remainder of the side-chain poly(alkylene oxide) units can comprise alkylene oxide and substituted alkylene oxide units having from 3 to about 10 carbon atoms, such as propylene oxide, tetramethylene oxide, butylene oxides, epichlorohydrin, epibromohydrin, allyl glycidyl ether, styrene oxide, and the like, and mixtures thereof. The term "final polyurethane" means the polyurethane produced after formation of the prepolymer followed by the chain extension step as described more fully hereafter.

Compounds of poly(alkylene oxide) side-chains are known to those skilled in the art. For example, active hydrogen-containing compounds include various diols having repeat units of poly(alkylene oxide) side-chains (e.g. from about 5 to about 50 and desirably from about 15 or about 20 to about 30 or about 40) such as those described in U.S. Pat. No. 3,905,929 (hereby incorporated herein by reference in its entirety). Further, U.S. Pat. No. 5,700,867 (hereby incorporated herein by reference in its entirety) teaches methods for incorporation of poly(ethylene oxide) side-chains at col. 4, line 35 to col. 5, line 45. A preferred active hydrogen-containing compound having poly(ethylene oxide) side-chains is trimethylol propane monoethoxylate methyl ether, available as Tegomer D-3403 from Degussa-Goldschmidt. Tegomer D-3403 generally has an average side chain degree of polymerization of from about 15 to about 35 and desirably from about 22 to about 28 predominately ethylene oxide repeat units. The number average molecular weight of the preferred side-chain containing alkylene oxide monomers is generally from about 350 to about 5,000, and preferably from about 750 to about 2,000.

Another class of nonionic dispersants include diisocyanates having pendent polyoxyethylene chains which may be used in the preparation of the nonionic prepolymer include those described in the prior art, for example in U.S. Pat. No. 3,920,598, hereby fully incorporated by reference. These diisocyanates, because of their function, may be regarded as dispersing diisocyanates. Particularly suitable dispersing diisocyanates may be obtained by reacting two moles of an organic diisocyanate in which the two isocyanate groups have different reactivities with approximately one mole of a polyethylene glycol mono-ether, the initially formed urethane monoisocyanate then reacting at a higher temperature with the excess diisocyanate to form an allophanate diisocyanate having a pendent polyoxyethylene chain.

While either an ionic or a nonionic dispersant can be utilized, it is within the ambit of the present invention to utilize blends or mixtures of both ionic or nonionic dispersants, as well as a dispersant which contain an ionic and a nonionic group or segment to achieve desired stable polyurethane dispersions.

Catalysts

Generally any conventional thermoplastic polyurethane catalyst known to the literature and to the art can be utilized in preparing the thermoplastic polyurethane of the present invention. Such catalysts include organic and inorganic acid salts of, and organometallic derivatives of, bismuth, tin, iron, antimony, cobalt, thorium, aluminum, zinc, nickel, cerium, molybdenum, vanadium, copper, manganese and zirconium, as well as phosphines, tertiary organic amines, and multifunctional polyalcohol amine catalysts. Representative organotin catalysts have from about 6 to about 20 carbon atoms and include stannous octoate, dibutyltin dioctoate, dibutyltin diluarate, and the like. Representative tertiary organic amine catalysts include triethylamine, triethylenediamine, N,N,N'N'-tetramethylethylenediamine, N,N,N'N'-tetraethylethylenediamine, N-methyl-morpholine, N-ethylmorpholine, N,N,N',N'-tetramethylguanidine, N,N,N',N'-tetramethyl-1,3-butanediamine, N,N-dimethylethanolamine, N,N-diethylethanol-amine, diazabicyclo[2.2.2]octane, and the like. Representative polyalcohol amine catalysts include triethanolamine, diethanolamine, or bis(2-hydroxyethyl)amino-2-propanol, and the like.

The amount of catalyst employed is generally less than about 1000 and desirably less than about 400 parts by weight per million parts by weight of the total weight of the polyurethane forming reactants, i.e., polyisocyanate(s), the hydroxyl-terminated thiocarbonates whether or not they contain vinyl repeat units therein, and the chain extenders. Mixtures of the above noted catalysts can likewise be utilized. It is desirable to use minimal amounts of the catalyst in order to minimize side reactions. Preferred catalysts include stannous octoate, dibutyltin dioctoate, dibutyltin dilaurate, and bismuth octoate.

Active Hydrogen Compounds or Isocyanate Reactive Compounds

Although optional, it is an important aspect of the invention that active hydrogen or isocyanate reactive compounds, such as polyols, can be utilized in addition to the above-noted hydroxyl-terminated thiocarbonates whether or not they contain vinyl or other repeat units therein. The use of such active hydrogen or isocyanate reactive compounds is often desirable with regard to achieving suitable polyurethane end properties and occasionally can serve as a dispersant or a quasi dispersant. The term "polyol" denotes any high molecular weight compound, other than the hydroxyl terminated thiocarbonate compounds, polymers, and copolymers, such as polymers having an average of about two or more hydroxyl groups per molecule. Examples of such polyols that can be used in the present invention include so-called simple or substantially polyhydroxyl hydrocarbon polyols (preferred), as well as other polymeric polyols such as polyester polyols and polyether polyols, as well as polyhydroxy polyester amides, hydroxyl-containing polycaprolactones, hydroxyl-containing acrylic interpolymers, hydroxyl-containing epoxides, polyhydroxy polycarbonates, polyhydroxy polyacetals, polyhydroxy polythioethers, polysiloxane polyols, ethoxylated polysiloxane polyols, polybutadiene polyols and hydrogenated polybutadiene polyols, polyacrylate polyols, halogenated polyesters or halogenated polyethers, and the like, and mixtures thereof. The polyester polyols, polyether polyols, polycarbonate polyols, and polysiloxane polyols are preferred.

The so-called hydrocarbon polyols are generally diols having from 2 to about 12 or about 20 carbon atoms and preferably 2 to about 4 or about 6 or about 10 carbon atoms and include ethylene glycol, 1,2- and 1,3-propylene glycols, 1,2-, 1,3-, 1,4-, and 2,3-butylene glycols, hexane diols, neopentyl glycol, 1,6-hexanediol, 1,8-octanediol, and other glycols such as bisphenol-A, cyclohexane diol, cyclohexane dimethanol (1,4-bis-hydroxymethylcyclohexane), 2-methyl-1,3-propanediol, 2,2,4-trimethyl-1,3-pentanediol, halogenated diols, and the like, and mixtures thereof. Preferred diols include ethylene glycol, diethylene glycol, propylene glycol, butylene glycol, hexane diol, and neopentyl glycol.

The polyester polyols typically are esterification products prepared by the reaction of organic polycarboxylic acids or their anhydrides with a stoichiometric excess of a diol. The diols used in making the polyester polyols include alkylene glycols having from 2 to about 20 total carbon atoms, e.g., ethylene glycol, 1,2- and 1,3-propylene glycols, 1,2-, 1,3-, 1,4-, and 2,3-butylene glycols, hexane diols, neopentyl glycol, 1,6-hexanediol, 1,8-octanediol, and other glycols such as bisphenol-A, cyclohexane diol, cyclohexane dimethanol (1,4-bis-hydroxymethylcyclohexane), 2-methyl-1,3-propanediol, 2,2,4-trimethyl-1,3-pentanediol, diethylene glycol, triethylene glycol, tetraethylene glycol, polyethylene glycol, dipropylene glycol, polypropylene glycol, dibutylene glycol, polybutylene glycol, dimerate diol, hydroxylated bisphenols, polyether glycols, halogenated diols, and the like, and mixtures thereof. Preferred diols include ethylene glycol, diethylene glycol, butylene glycol, hexane diol, and neopentyl glycol. Suitable carboxylic acids used in making the polyester polyols generally have from 1 to about 20 total carbon atoms and include dicarboxylic acids (preferred) and tricarboxylic acids and anhydrides, e.g., maleic acid, maleic anhydride, succinic acid, glutaric acid, glutaric anhydride, adipic acid (preferred), suberic acid, pimelic acid, azelaic acid, sebacic acid, chlorendic acid, 1,2,4-butane-tricarboxylic acid, phthalic acid, the isomers of phthalic acid, phthalic anhydride, fumaric acid, dimeric fatty acids such as oleic acid, and the like, and mixtures thereof.

The preferred polyester polyol has two hydroxyl end groups. Preferred polyester diols include poly(butanediol adipate); hexane diol adipic acid and isophthalic acid polyesters such as hexane adipate isophthalate polyester; hexane diol neopentyl glycol adipic acid polyester diols, and neopentyl glycol adipic acid.

Polythioether polyols which can be used include products obtained by condensing thiodiglycol either alone or with other glycols, dicarboxylic acids, formaldehyde, minoalcohols or aminocarboxylic acids.

Polyether diols may be substituted in whole or in part for the polyester diols. Polyether polyols contain from 2 to about 15 carbon atoms in the repeat unit and are obtained in known manner by the reaction of (A) the starting compounds that contain reactive hydrogen atoms, such as water or the diols set forth for preparing the polyester polyols, and (B) alkylene oxides, such as ethylene oxide, propylene oxide, butylene oxide, styrene oxide, tetrahydrofuran, epichlorohydrin, and the like, and mixtures thereof. Preferred polyethers include poly(propylene glycol), polytetrahydrofuran, and copolymers of poly(ethylene glycol) and poly(propylene glycol).

Polycarbonates include those obtained from the reaction of (A) diols such 1,3-propanediol, 1,4-butanediol, 1,6-hexanediol, diethylene glycol, triethylene glycol, tetraethylene glycol, and the like, and mixtures thereof with (B) diarylcarbonates such as diphenylcarbonate or phosgene.

Polyacetals include the compounds that can be prepared from the reaction of (A) aldehydes, such as formaldehyde and the like, and (B) glycols such as diethylene glycol, triethylene glycol, ethoxylated 4,4'-dihydroxy-diphenyldimethylmethane, 1,6-hexanediol, and the like. Polyacetals can also be prepared by the polymerization of cyclic acetals.

The aforementioned diols useful in making polyester polyols can also be used as additional reactants to prepare the isocyanate terminated prepolymer.

Of the above various one or more polyols which can be utilized, generally the hydrocarbon polyols, polyether polyols, polyester polyols; and polyhydroxy polycarbonates are preferred. The above-noted optional polyols can be utilized in association with a hydroxyl-terminated thiocarbonates in an amount of from about 0 or about 0.1 to about 80, desirably from about 1 to about 50 and preferably from about 2 to about 20 parts by weight per 100 total parts by weight of the final formed polyurethane.

Urethane Reaction Temperatures

The polyurethane forming reaction is performed at temperatures generally from about 30° C. to about 220° C., desirably from about 40° C. to about 120° C., and preferably from about 50° C. to about 100° C. Temperatures above about 220° C. are generally avoided in order to prevent the polyurethanes from decomposing. Suitable mixing times in order to enable the various components to react and form the thermoplastic polyurethanes of the present invention are generally from about 1 to about 5 and desirably from about 2 to about 3 minutes.

Prepolymer and Polymer Preparation Routes

The preparation of a urethane prepolymer and/or polymer can generally be carried out according to one of three routes, that is a waterborne route, a solvent route, or a bulk route.

Waterborne Route-Neutralization

Considering the waterborne route, one or more of the above noted ionic dispersants are utilized and the same must be neutralized generally before or during addition of the urethane prepolymer to water. Neutralization via the waterborne route involves, for example, converting the pendant carboxyl groups of an ionic (e.g. acid dispersant to a carboxylate anion, in the prepolymer, which has a water dispersability enhancing effect. Suitable neutralizing agents for the prepolymers are desirably tertiary amines having a total of from 1 to about 20 carbon atoms and desirably from about 1 to about 5 carbon atoms. Examples of suitable tertiary amines include triethyl amine (TEA), dimethyl ethanolamine (DMEA), N-methyl morpholine, and the like. Primary or secondary amines can also be used in lieu of tertiary amines if they are sufficiently hindered to avoid interfering with the chain extension process. Alternatively, alkaline hydroxides such as sodium hydroxide, potassium hydroxide, or ammonium hydroxide can be used.

A preferred neutralization route is to first neutralize the urethane prepolymers containing an anionic dispersant therein and then subsequently add the same to water. A less preferred route is to add the neutralizing compound such as a tertiary amine to water and then to add the urethane prepolymer thereto. An amount of water is generally utilized such that an aqueous dispersion of the urethane prepolymer exists. Thus, an amount of water can be utilized to obtain a desired solids content after chain extension and/or crosslinking via the waterborne route such as from about 10 to about 70 and desirably from about 30 to about 55% by weight after chain extension.

Waterborne Route-Chain Extension

The active hydrogen-containing chain extender which is reacted with the waterborne prepolymer is desirably an amine because of its high rate of reactivity versus a diol or water, (which is a competing reaction). Suitable long-chain amines include polyester amides and polyamides, such as the predominantly linear condensates obtained from reaction of (A) polybasic saturated and unsaturated carboxylic acids or their anhydrides, and (B) polyvalent saturated or unsaturated aminoalcohols, diamines, polyamines, and the like, and mixtures thereof. Desired amine compounds include an amino alcohol, ammonia, a primary or secondary aliphatic, alicyclic, aromatic, aralipathic or heterocyclic amine having a total of from about 2 to about 20 carbon atoms, especially a diamine, urea or derivatives thereof, hydrazine or a substituted hydrazine. Water-soluble chain extenders are preferred.

Examples of suitable chain extenders useful herein include ethylene diamine (EDA), diethylene triamine (DETA), triethylene tetramine (TETA), propylene diamine, butylene diamine, hexamethylene diamine, cyclohexylene diamine, piperazine, 2-methyl piperazine, phenylene diamine, 2-methylpentamethylenediamine, tolylene diamine, xylylene diamine, tris(2-aminoethyl) amine, 3,3'-dinitrobenzidine, 4,4'-methylenebis (2-chloroaniline), 3,3'-dichloro-4,4'-biphenyl diamine, 2,6-diaminopyridine, 4,4'-diaminodiphenylmethane, menthane diamine, m-xylene diamine and isophorone diamine. Also materials such as hydrazine, azines such as acetone azine, substituted hydrazines such as, for example, dimethyl hydrazine, 1,6-hexamethylene-bis-hydrazine, carbodihydrazine, hydrazides of dicarboxylic acids and sulfonic acids such as adipic acid mono- or dihydrazide, oxalic acid dihydrazide, isophthalic acid dihydrazide, tartaric acid dihydrazide, 1,3-phenylene disulfonic acid dihydrazide, and omega-amino-caproic acid dihydrazide. Hydrazides made by reacting lactones with hydrazine such as gamma-hydroxyl-butyric hydrazide, bis-semi-carbazide, and bis-hydrazide carbonic esters of glycols such as any of the glycols mentioned above, and the like.

Where the chain extender is other than water, for example a diamine or hydrazine, it may be added to the aqueous dispersion of prepolymer or, alternatively, it may already be present in the aqueous medium when the prepolymer is dispersed therein or added simultaneously.

The chain extension of the waterborne urethane prepolymers can be conducted at elevated, reduced or ambient temperatures. Convenient temperatures are from about 5° C. to 95° C. or more, preferably from about 10° C. to about 45° C.

With respect to waterborne systems, the ratio of the total number of equivalents of Zerewitinoff active hydrogen groups of all chain extenders utilized as compared to the total number of equivalents of isocyanate groups ranges generally from about 0.1 to about 2.0, desirably from about 0.15 to about 1.5, and preferably from about 0.3 to about 1.1. Of course, when water is utilized as a chain extender, the above ratios are not applicable since as well known to the art and to the literature, water can function both as a chain extender and a dispersing medium and will be present in a large excess relative to the amount of free NCO groups.

Solvent Route

The various thermoplastic polyurethanes can be prepared by polymerization of the various components, for example an isocyanate compound, the hydroxyl terminated thiocarbonate, various active hydrogen compounds such as polyether diol, etc., and the like, in a solvent. Desired solvents include volatile hydrocarbons such as the various alkanes having from 5 to about 17 carbon atoms, for example pentane, hexane, heptane, octane, and the like, or various aromatic or hydrocarbons containing both an aromatic ring and an aliphatic group such as benzene, toluene, xylene, and the like. Another group of suitable solvents are the various acetates wherein the ester portion contains from 1 to about 5 carbon atoms with examples including methyl acetate, ethyl acetate, and the like. Various ketones having from about 3 to about 10 carbon atoms can also be utilized such as acetone, methyl ethyl ketone, and the like. Polymerization of the various urethane forming components such as the prepolymer components are carried out in the solvent at suitable temperatures using suitable catalysts to generally form a urethane prepolymer.

Solvent Route-Chain Extension

Chain extension of the various urethane prepolymers generally utilizes hydroxyl terminated chain extenders known to the literature and to the art such as various organic diols or glycols having a total of from 2 to about 20 carbon atoms such as alkane diols, cycloaliphatic diols, alkylaryl diols, and the like. Alkane diols which have a total from about 2 to about 6 carbon atoms are often utilized with examples including ethanediol, propane glycol, 1,6-hexanediol, 1,3-butanediol, 1,5-pentanediol, neopentylglycol, and preferably 1,4-butanediol. Dialkylene ether glycols having from 4 to about 20 carbon atoms, can also be utilized such as diethylene glycol and dipropylene glycol. Examples of suitable cycloaliphatic diols include 1,2-cyclopentanediol, 1,4-cyclohexanedimethanol (CHDM) and the like. Examples of suitable alkylaryl diols include hydroquinone di(β-hydroxyethyl) ether (HQEE), 1,4-benzenedimethanol, bisethoxy biphenol, bisphenol A ethoxylates, bisphenol F ethoxylates and the like. Still other suitable chain extenders are 1,3-di (2-hydroxyethyl) benzene, and 1,2-di(2-hydroxyethoxy) benzene. Mixtures of chain extenders can also be utilized.

Suitable hydroxyl-functional chain extenders of the present invention include 1,4-butanediol, ethylene glycol, diethylene glycol, 1,6-hexane diol, 1,4-cyclohexanedimethanol (CHDM), hydroquinone di(β-hydroxyethyl) ether (HQEE), and 1,4-benzenedimethylol.

If an increase in molecular weight of the urethanes formed via a solvent route is desired, any residual isocyanate groups can be reacted with various diamines as set forth hereinabove with regard to the waterborne route such as EA, DETA, or TETA, and the like. Alternatively, multi-functional chain extenders can be utilized such as trimethylol propane, glycerol, pentaerythritol, 1,2,6-hexanetriol, N,N,N-triethanolamine, N,N-diethanolamine, trimethylolethane, and diethylenetriamine. Combinations of chain extenders can be utilized. The amount of multi-functional isocyanate components, e.g. multi-functional chain extenders, catalysts, and/or polyols utilized to form the polyurethanes is limited so that the polymer remains soluble and at a reasonable processing and handling viscosity.

Bulk Polymerization Route

Another route to prepare the various thermoplastic urethane or urethane prepolymers is via bulk polymerization such as in a reaction vessel or an extruder. According to this route, the various urethane forming components such as the isocyanate reactive compounds, e.g. one or more polyols, one or more thiocarbonate compounds, one or more chain extenders, one or more functional modifiers, and the like are mixed together along with one or more isocyanates and heated to a suitable reaction temperature to form a thermoplastic polyurethane composition.

Branched or precrosslinked urethane polymers are readily formed by utilizing polyisocyanates having 3 or 4 isocyanate groups and/or active hydrogen compounds such as the various above listed polyols having at least three functional groups such as a hydroxyl group thereon. Chain extenders and/or various dispersants can also be utilized having 3, 4 or more isocyanate reactive functional end groups. Such compounds are known to the art and to the literature.

Thermoplastic Polyurethanes and Formation Routes Thereof

The thermoplastic polyurethanes of the present invention whether prepared via a waterborne dispersion, a solution or bulk polymerization can be conducted by several different routes which are briefly summarized and then more fully described. Polyurethanes are generally formed by reacting 1) one or more isocyanates; 2) one or more hydroxyl-terminated thiocarbonate compounds, polymers, or copolymers; 3) optionally, one or more isocyanate reactive polyols; 4) optionally, one or more chain extenders; and 5) optionally a catalyst.

A prepolymer route can be utilized wherein a hydroxyl terminated thiocarbonate copolymer component containing repeat groups therein derived from a conjugated diene and/or a vinyl monomer, optionally a polyol, and optionally a dispersant, are reacted with a polyisocyanate optionally in the presence of a catalyst to form an isocyanate terminated prepolymer, which is subsequently chain extended. The polyurethane can either be solvent borne or waterborne. A second route relates to a polyurethane prepolymer made by using various conjugated diene and/or vinyl monomers as a diluent for the hydroxyl-terminated thiocarbonated compound, polymer, or copolymer component, optionally a polyol, a dispersant, a polyisocyanate, and an optional catalyst are all added together, mixed, and reacted. The polymer can be neutralized and dispersed in water and optionally chain extended. The vinyl and/or diene monomers are then reacted into the backbone of the thiocarbonate in the presence of an initiator. A third route relates to reacting a polyol and a dispersant (e.g., a waterborne acrylic) with a diisocyanate to form a prepolymer which is subsequently reacted with one or more thiocarbonate compounds to form a thiocarbonate end capped urethane block. Similar to Route 2, vinyl containing monomers can be utilized as reactive diluents. The prepolymer is then neutralized and dispersed into water. Various vinyl monomers and/or conjugated diene monomers are then in situ polymerized to form block copolymers such as an ABA block copolymer, if desired.

Regardless of the reaction route, various vinyl and/or conjugated diene monomers can exist as repeat units within the thiocarbonate compound before it is reacted; or be initially contained within the mixture, or subsequently added after formation of a dispersion and then reacted into the backbone of the thiocarbonate compound.

Prepolymer Route

One polyurethane formation route involves a prepolymer route for preparing a urethane-acrylic copolymer dispersion utilizing a polyacrylate polyol prepared from a hydroxyl functional thiocarbonate compound previously described, an anionic dispersant, a polyisocyanate, and optionally a non-reactive organic solvent which can be utilized to control the viscosity of the prepolymer. In this route, all of the above desired ingredients are added to reaction vessel and reacted with a catalyst optionally being added with the above ingredients or after partial reaction thereof. The prepolymer is subsequently neutralized as by an amine followed by the addition to/or of water. Chain extension can then be carried out. This route utilizes a hydroxyl-terminated thiocarbonate compound such as any of those set forth in Block Formulas AA, BB, CC, or EE where j equals 1 or 2 containing repeat groups derived from the one or more conjugated dienes and/or the one or more vinyl-containing monomers such as vinyl acetates. Preferred conjugated diene or vinyl compounds which can be utilized included styrene or an acrylate wherein the ester portion contains from 1 to about 10 carbon atoms such as ethylacrylate, butylacrylate, or 2-ethylhexylacrylate.

Various solvents can be utilized with organic solvents being desired as noted above with N-methylpyrrolidone being preferred.

Optionally, one or more active hydrogen or isocyanate reactive compounds such as a polyol can be utilized. Such polyols are set forth hereinabove with the hydrocarbon polyols, polyester polyols, polycarbonate polyols, and the polyether polyols such as tetramethyleneoxide polyol which is preferred.

The isocyanate utilized to form a prepolymers is generally a diisocyanate as set forth hereinabove. Thus, generally any of the above-noted aliphatic polyisocyanates, the cycloaliphatic polyisocyanates, or the aromatic polyisocyanates can be utilized with the cycloaliphatic polyisocyanates being preferred such as dicyclohexylmethane diisocyanate and isophorone diisocyanate.

The formation of the urethane-acrylic copolymer prepolymer is formed by combining the above-noted compounds and heating at an elevated temperature such as from about 30° C. to about 100° C. and desirably from about 40° C. to about 90° C. An excess of the polyisocyanate is preferably utilized for subsequent chain extension. If a waterborne dispersion has been formed, desirably amine type chain extenders are utilized whereas if the prepolymer was formed by solution polymerization, diol type chain extenders are utilized. During the prepolymer formation, a urethane catalyst can be utilized as noted hereinabove or optionally, the prepolymer reaction can be partially carried out at which time a catalyst such as a tin catalyst can be added.

Once the urethane dispersion derived from a thiocarbonate-vinyl copolymer has been formed, it can be chain extended utilizing any of the above-noted chain extenders set forth herein with hydrazine being preferred. Alternatively, the chain extender can be contained in the water which is preferable with aromatic isocyanate based prepolymers.

Various nuances of the above prepolymer dispersion route of forming a polyurethane derived from a thiocarbonate-acrylate copolymer can be utilized. For example, if a dispersion is not desired but only a solvent borne urethane thiocarbonate-acrylic polymer, a neutralizing agent and water is not utilized but only the above-noted solvents which are then required in additional amounts to control the viscosity of the final molecular weight of the composition. Another option is that if a pre-crosslinked polymer or copolymer is desired, it can be achieved by a number of ways such as by utilizing a polyol, or an isocyanate, or even a chain extender having a functionality of at least three, alone or in combination with a difunctional chain extender. Crosslinking can also be achieved by post addition of crosslinkers.

The following examples with respect to the preparation of a polyurethane dispersion by essentially adding all of the components together serves to illustrate, but not to limit the present invention.

EXAMPLE 11

A prepolymer was prepared by combining all of the ingredients below except the catalysts at 60° C. to a 4 neck flask equipped with a thermometer, overhead stirrer and gas inlet. The temperature of the reaction mixture was raised to 84° C.-86° C. and held at this temperature for 30 minutes. The catalyst was then added at 84° C.-86° C. and the temperature held there for another 1.5 hours or until theoretical NCO % was reached as indicated by titration of a small sample.

| Material | Parts - Wt |
|---|---|
| Ethyl acrylate polyol (from RAFT diol)-Formula EE where $R^4$ and $R^5$ are methyl, $R^{13}$ is <br> —N⟨piperazine⟩N—, <br> and $R^{14}$ is ethylene, (OH# = 43.5) | 280 |
| Dimethylolpropionic Acid | 20.8 |
| N-methylpyrrolidone | 80 |
| Isophorone diisocyanate | 117 |
| T9, tin di-octonate catalyst | 0.1 |

A polyurethane dispersion was prepared by neutralizing the above prepolymer with 16.4 parts of triethylamine at 68° C. to 70° C. and dispersing the neutralized prepolymer in water while maintaining the water/dispersion temperature below 28° C. The dispersed prepolymer was extended with hydrazine to give a 40.4% solids polyurethane dispersion with low sediment, a viscosity of 170 cps (at 25° C.) at a pH of 7.5.

EXAMPLE 12

The following is an example of the use of an acetone functional acrylic polyol prepared from ethyl acrylate and diacetone acrylamide using the RAFT diol (dithiocarbonate based) to prepare a self-crosslinking urethane-acrylic copolymer.

A prepolymer was prepared by combining all of the ingredients below except the catalyst at 60° C. to a 4 neck flask equipped with a thermometer, overhead stirrer and gas inlet. The temperature of the reaction mixture was raised to 84° C. to 86° C. and held at this temperature for 30 minutes. The catalyst was then added at 84° C. to 86° C. and the temperature held there for another 1.5 hours or until theoretical NCO % was reached as indicated by titration of a small sample.

| Material | Parts - Wt |
|---|---|
| Ethyl acrylate/diacetone acrylamide based polyol (from RAFT diol)-Formula EE where $R^4$ and $R^5$ are methyl, $R^{13}$ is <br> —N⟨piperazine⟩N—, <br> and $R^{14}$ is ethylene, (OH# = 39.7) | 120 |
| Tetramethyleneoxide polyol (OH# = 38.6) | 120 |
| Dimethylolpropionic Acid | 18.2 |
| N-methylpyrrolidone | 67 |
| 4,4'-methylene bis(cyclohexyl) diisocyanate | 117 |
| T9, tin di-octonate catalyst | 0.1 |

A polyurethane dispersion was prepared by neutralizing the above prepolymer with 14.4 parts of triethylamine at 68° C.-70° C. and dispersing the neutralized prepolymer in water while maintaining the water/dispersion temperature below 28° C. The dispersed prepolymer was extended with hydrazine to give a 43.6% solids polyurethane dispersion with low sediment, a viscosity of 105 cps (at 25° C.) at a pH of 9.3. To this dispersion adipic acid dihydrazide (ADH) was added to render it self-crosslinking.

Prepolymer Route-"In-Situ" Acrylic Urethane Polymerization

Another route with regard to the preparation of a urethane thiocarbonate-vinyl copolymer comprises mixing all the various reactant components together utilizing a conjugated diene and/or a vinyl monomer such as an acrylate as a diluent, desirably with a dispersant and optionally a polyol, and reacting the same with a isocyanate to form a polyurethane prepolymer. The composition is then neutralized with a tertiary amine if required, dispersed in water, and generally subsequently chain extended. Then, the diluent such as acrylate and/or styrene monomers are polymerized into the thiocarbonate unit utilizing a free radical initiator. This route permits the size of the thiocarbonate vinyl block to be tailor made, permits formation of uniform high molecular weight acrylate blocks, and desirable properties typically associated with acrylic polymers such as weatherability, chemical and solvent resistance, adhesion, and flexibility with respect to a desired Tg. Moreover, this approach is more economical in that a separate polyol preparation step is not required and the monomer can act as a solvent for the prepolymer eliminating the need of processing solvents.

The preparation of the polyurethane dispersion using various monomers such as conjugated dienes or vinyl containing monomers as a diluent is carried out utilizing many of the same components set forth hereinabove as well as in the immediately above described urethane prepolymer route and are hereby fully incorporated by reference. Hence, the procedure will not be repeated herein.

An essential reaction component of the present route is the utilization of a hydroxyl-terminated thiocarbonate discussed hereinabove such as those set forth in Formulas AA, BB, CC, and EE wherein j equals 1 or 2 and thus are fully incorporated by reference. As noted, these thiocarbonates desirably do not have any units derived from a conjugated diene or a vinyl monomer therein.

Any of the polyols previously described can optionally be utilized in the prepolymer preparation.

Since a polyurethane dispersion is made, either an ionic or nonionic dispersant is utilized with the above noted acid dispersants being preferred such as the dihydroxy-carboxylic acids.

Rather than utilizing a solvent, various reactive monomers such as a conjugated diene monomer and/or one or more vinyl containing monomers such as the various acrylates are utilized as a diluent and the same can be subsequently polymerized into the polyurethane to form the urethane thiocarbonate-vinyl copolymer. These monomers are set forth hereinabove and are thus hereby incorporated by reference. The vinyl containing monomers are desired with a styrene type and the acrylates or methacrylates generally having from 1 to 18 carbon atoms in the ester portion being preferred.

The above noted various types of polyisocyanates are utilized with diisocyanates being highly preferred such as the aliphatic polyisocyanates, the cycloaliphatic polyisocyanates, aromatic polyisocyanates, and the like with the cycloaliphatic polyisocyanates being highly preferred.

The reaction of the various hydroxyl-containing components with the diisocyanates is carried out in a manner as set forth hereinabove utilizing suitable urethane catalysts such as the various tin catalysts described above. Naturally, an excess of the isocyanate is utilized so that the polymers substantially contain isocyanate end groups for subsequent reaction as by chain extending.

In order to form a dispersion, the active groups of the ionic type dispersants are neutralized and thus with regard to an acid dispersion, the same are neutralized using various basic compounds as noted hereinabove such as the various tertiary amines, ammonium hydroxide, and the like. Generally neutralization is followed by or occurs simultaneously with addition of the neutralized polymer to water to form an aqueous dispersion of the urethane polymers.

The various diluent monomers are then polymerized utilizing free radical initiators as noted hereinabove such as various azo compounds, peroxides, peroxyesters, and the like. An important advantage of the present route is that the urethane thiocarbonate-acrylate copolymers can be tailor made with regard to the size of the incorporated monomer such as styrene or an acrylate by the amount thereof utilized as a diluent versus the raft (thiocarbonate) diol. Uniform block copolymers of the styrene and/or the acrylate can thus be made. Hence, chemical and physical properties of the end copolymer can also be controlled such as hardness, solvent resistance, functionality, and the like. The polyurethanes can possess the advantages of acrylic polymers such as weatherability, adhesion and resistant properties. The diluent monomers when polymerized are incorporated into the thiocarbonate compounds between the sulfur atom and the adjacent

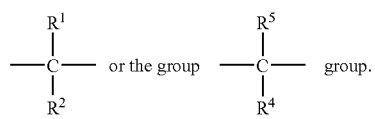

An example of such is Block Formula AA as is set forth hereinabove. Naturally, a portion of the urethane copolymer will contain a structure as set forth in Block Formulas AA, BB, CC, and EE where j equals 1 or 2. Preferred diluent monomers include styrene, an alkylacrylate, or an alkylmethacrylate, wherein the alkyl has from 1 to about 30carbon atoms such as ethylacrylate, butylacrylate, and the like.

Nuances of the above general description of the preparation of a polyurethane dispersion utilizing various monomers as a diluent includes the utilization of adding additional conjugated diene and/or vinyl monomer before polymerization, or after dispersing the urethane prepolymer, particularly after chain extension. Thus, relatively low viscosity dispersions can be prepared and then a desired amount of additional conjugated diene and/or vinyl type monomer such as acrylate can be added to achieve desirable blocks within the thiocarbonate as well as to achieve desired end properties. Another nuance is that various crosslinking agents can be added either during or after chain extension to form a pre-crosslinked/branched product. When a solvent borne urethane thiocarbonate-acrylic copolymer is desired, a dispersant is not utilized but rather one or more solvents which generally do not enter into the polymerization reaction. Such solvents are described hereinabove and include compounds such as various alkanes, acetone, aromatic hydrocarbons, N-methylpyrrolidone, acetate amides such as dimethyl formamide, and the like.

The invention will be better understood by the following examples which serve to illustrate but not to limit the present invention.

EXAMPLE 13

A prepolymer was prepared by adding all of the ingredients below except the catalysts at 60° C. to a 4 neck flask equipped with a thermometer, overhead stirrer and gas inlet. The temperature of the reaction mixture was raised to 84° C.-86° C. and held at this temperature for 30 minutes. The catalyst was then added at 84° C.-86° C. and the temperature held there for another 1.5 hours or until theoretical NCO % was reached as indicated by titration of a small sample.

| Material | Parts - Wt |
|---|---|
| Tetramethyleneoxide polyol (OH# = 38.6) | 174.3 |
| RAFT diol-Formula EE where $R^4$ and $R^5$ are methyl, $R^{13}$ is | 48.9 |

$$-N\diagup\!\!\!\diagdown N-,$$

| and $R^{14}$ is ethylene, (OH# = 225.3) | |
|---|---|
| Dimethylolpropionic Acid | 18.2 |
| Methyl Methacrylate | 111 |
| Butyl Acrylate | 13 |
| Isophorone diisocyanate | 130.6 |
| Tin di-octonoate catalyst | 0.1 |

A polyurethane dispersion was prepared by neutralizing the above prepolymer with 16.4 parts of triethylamine at 68° C.-70° C. and then dispersing the neutralized prepolymer in water using high speed stirring while maintaining the water/dispersion temperature below 28° C. With continued stirring the dispersed prepolymer was extended with hydrazine. Polymerization of the acrylic was effected by adding 0.3 parts of a 1% Fe (EDTA) solution, then adding 5 parts of a 2% erythorbic acid solution neutralized with triethylamine then subsequently adding 3 parts of a 3.5% t-butyl hydroperoxide solution and (heated at 34° C.-36° C.). The resulting polymeric dispersion has a solids content of 46.5% with a low level of sediment, a viscosity of 100 cps (at 250° C.) at a pH of 8.4.

EXAMPLE 14

The following is an example of the preparation of a "pure" urethane-acrylic copolymer (without other soft segment polyol based raw materials) using the RAFT diol and acrylic monomers to create the soft-segment for the polyurethane.

A prepolymer was prepared by charging all of the ingredients below to a 4 neck flask equipped with a thermometer, overhead stirrer and gas inlet. The temperature of the reaction mixture was raised to 84° C.-86° C. and held at this temperature for 2 hours. The temperature held until the theoretical NCO % was reached as indicated by titration of a small sample.

| Material | Parts-Wt |
|---|---|
| RAFT diol-Formula EE where $R^4$ and $R^5$ are methyl, $R^{13}$ is  and $R^{14}$ is ethylene, (OH# = 225.3) | 20.7 |
| Butane diol | 28.3 |
| Dimethylolbutanoic Acid | 27.0 |
| Methyl methacrylate | 46 |
| Butyl acrylate | 184 |
| Isophorone diisocyanate | 153.9 |

A polyurethane dispersion was prepared by neutralizing the above prepolymer with 20.2 parts of triethylamine at 68° C.-70° C. and then dispersing the neutralized prepolymer in water using high speed stirring while maintaining the water/dispersion temperature below 28° C. With continued stirring the dispersed prepolymer was extended with hydrazine. Polymerization of the acrylic was carried out by adding 0.3 parts of a 1% Fe (EDTA) solution and 3 parts of a 3.5% t-butyl hydroperoxide solution, heating to 34° C.-36° C. and then adding 5 parts of a 2% erythorbic acid solution neutralized with triethylamine. The resulting polymeric dispersion has a solids content of 34.5% with a low level of sediment, a viscosity of 50 cps (at 25° C.) at a pH of 7.5.

Thiocarbonate Capped Prepolymer Route

Still another polyurethane formation route relates to forming various block copolymers such as AB or $(AB)_nA$ blocks containing at least one thiocarbonate or acrylic "A" block as well as at least one urethane "B" block, where n is from 1 to about 20 and desirably from 1 to about 5. This route generally involves the reaction of at least one polyol and an anionic dispersant and an excess amount of a diisocyanate to form a polyurethane prepolymer, in the presence of a conjugated diene or vinyl monomer diluent. Subsequently, the urethane prepolymer is reacted with one or more of the hydroxyl terminated thiocarbonate compounds set forth in Formulas AA, BB, CC, and EE where j equals 1 or 2, preferably 1, to produce a polyurethane prepolymer generally having terminal thiocarbonate compounds containing no conjugated diene or vinyl repeat units therein. The prepolymer is then neutralized and dispersed in water. The various acrylate monomers can then be polymerized in situ into the terminal thiocarbonate compounds in the presence of free radical initiators to yield a block copolymer such as an ABA wherein A is the thiocarbonate-acrylate block and B is a polyurethane block. According to this route, the size and molecular weight of the various blocks can be tailor made to yield suitable desired properties, such as molecular weight, flexibility, and hardness. Other advantages include the use of neutralizing agents which are more user friendly in that they are less volatile and offensive than conventional neutralizing agents such as TEA. Still another advantage is that the urethane prepolymer containing one or more thiocarbonate end groups can be stored, transported, moved to another location, or to an end user, etc., and optionally dispersed, then one or more conjugated diene and/or vinyl monomers added thereto such as styrene or an acrylate and polymerized into the thiocarbonate compounds via in-situ free radical polymerization. Still another advantage of the thiocarbonate end group containing urethane prepolymer is that different processes are available. For example, significantly higher prepolymer and water temperatures with respect to the dispersion step can be utilized as well as extended dispersion time (virtually unlimited) without loss of isocyanate end groups due to water side reactions since, of course, there are no isocyanate groups. This route is also particularly advantageous for aromatic isocyanates that are harder to disperse and more reactive towards water and typically leads to problems with sediment or dispersion quality. Generally, the thiocarbonate capped prepolymer route yields increased productivity and process flexibility with less off-grade product.

The invention will be better understood by the following examples which serve to illustrate but not to limit the present invention.

EXAMPLE 15

A prepolymer was prepared by combining all of the ingredients below except the T9 and mono-hydroxyl functional RAFT reagent at 60° C. to a 4 neck flask equipped with a thermometer, overhead stirrer and gas inlet. The temperature of the reaction mixture was raised to 84-86° C. and held at this temperature for 30 minutes. The T9 catalyst was then added at 84-86° C. and the temperature held there for another 1.5 hours. At this point the mono-hydroxyl functional RAFT reagent (DTC based) was added in an amount sufficient to cap the remaining isocyanate groups (as determined by titration) and the temperature held at 84-86° C. for another hour or until less than 0.1% NCO was reached as indicated by titration of a small sample.

| Material | Parts |
|---|---|
| Poly-tetramethylene oxide, 1,000 number average molecular weight (OH# = 38.6) | 119.3 |
| Dimethylolbutanoic Acid | 17.8 |
| MMA | 199.8 |
| BA | 66.6 |
| 4,4'-methylene bis(cyclohexyl) diisocyanate | 94.2 |
| T9, tin di-octonoate catalyst | 0.1 |
| Mono-hydroxyl functional RAFT - Formula CC where j = 1, $R^4$ and $R^5$ are methyl, $R^6$ and $R^7$ are methyl, and $R^{14}$ is ethylene | 34.9 |

A polyurethane dispersion was prepared by neutralizing the above prepolymer with 12.7 parts of triethylamine at 68-70° C. and then dispersing the neutralized prepolymer in de-ionized water using high speed stirring. Polymerization of the acrylic was effected by adding 0.5 parts of a 1%

Fe(EDTA) solution and 3 parts of a 3.5% t-butyl hydroperoxide solution, heating to 34-36° C. and then adding 5 parts of a 2% erythorbic acid neutralized with triethylamine. The resulting polymeric dispersion has a solids content of 43.7% with a low level of sediment, a viscosity of 230 cps (at 25° C.) at a pH of 7.7.

EXAMPLE 16

A prepolymer was prepared by combining all of the ingredients below except the mono-hydroxyl functional RAFT reagent at 60° C. to a 4 neck flask equipped with a thermometer, overhead stirrer and gas inlet. The temperature of the reaction mixture was raised to 45-50° C. and held at this temperature for 30 minutes. The temperature was then raised to 70-75° C. and held there for another 1.5 hours. At this point the mono-hydroxyl functional RAFT reagent (DTC based) was added in an amount sufficient to cap the remaining isocyanate groups (as determined by titration) and the temperature held at 70-75° C. for another hour or until theoretical NCO % was reached as indicated by titration of a small sample.

| Material | Parts |
| --- | --- |
| PPG 2025 polyol (OH# = 56) (polypropylene glycol polyol) | 119.3 |
| Dimethylolbutanoic Acid | 17.8 |
| MMA | 64.3 |
| BA | 192.8 |
| 4,4'-diphenyl-methylene diisocyanate (MDI, Mondur M) | 60.9 |
| Mono-hydroxyl functional RAFT reagent - Formula CC where j = 1, $R^4$ and $R^5$ are methyl, $R^6$ and $R^7$ are methyl, and $R^{14}$ is ethylene | 30.2 |

A polyurethane dispersion was prepared by neutralizing the above prepolymer with 12.7 parts of triethylamine at 68-70° C. (typically not feasible with aromatic isocyanate based prepolymers containing active NCO groups) and then dispersing the neutralized prepolymer in de-ionized water using high speed stirring while maintaining the water/dispersion temperature. After the prepolymer was dispersed, 7 parts of di-acetone acrylamide dissolved in 7 parts de-ionized water was added to the dispersion. Polymerization of the acrylic was effected by adding 0.3 parts of a 1% Fe(EDTA) solution and 2.5 parts of a 2% erythorbic acid neutralized with triethylamine 3.5% t-butyl hydroperoxide solution, heating to 38-40° C. and then adding 1.4 parts of a 3.5% t-butyl hydroperoxide solution. The resulting polymeric dispersion has a solids content of 31.3% with a low level of sediment, a viscosity of 30 cps (at 25° C.) at a pH of 7.6. Adipic acid dihydrazide can be added to the dispersion to render it self crosslinking.

EXAMPLE 17

A similar polyurethane dispersion was prepared to the previously described dispersion (Example 6) using the same prepolymer composition, but neutralizing the above prepolymer with 11.2 parts of Di-methyl ethanol amine at 68-70° C. (typically not feasible with aromatic isocyanate based prepolymers containing active NCO groups) and then dispersing the neutralized prepolymer in de-ionized water using high speed stirring while maintaining the water/dispersion temperature. After the prepolymer was dispersed, 7 parts of di-acetone acrylamide dissolved in 7 parts de-ionized water was added to the dispersion. Polymerization of the acrylic was effected by adding 0.3 parts of a 1% Fe(EDTA) solution and 2.5 parts of a 2% erythorbic acid solution neutralized with triethylamine 3.5% t-butyl hydroperoxide solution, heating to 38-40° C. and then adding 1.4 parts of a 3.5% t-butyl hydroperoxide solution. The resulting polymeric dispersion has a solids content of 31.8% with a low level of sediment, a viscosity of 110 cps (at 25° C.) at a pH of 8.0. Adipic acid dihydrazide can be added to the dispersion to render it self crosslinking.

Other Prepolymer Routes

Any of the above described preparation routes of course can be used in combination to attain particular results or combine the practical benefits of each. For example, an acrylic polyol can be prepared according to the first or prepolymer route and used as a component in the second or in-situ urethane-acrylic preparation route for the synthesis of the copolymer. While the above three basic routes have been utilized with respect to preferred embodiments of the present invention, it is to be understood that any of the other routes can also be utilized.

Polyurethane-Molecular Weight

The number average molecular weight of the polymerized thermoplastic polyurethanes of the present invention made by the various routes can broadly range from about 10,000 to about 2,000,000. In another aspect the number average molecular weight can range from about 20,000 to about 1,500,000, and in still another aspect from about 40,000 to about 500,000, unless crosslinked. The molecular weight of the polymers of the invention is measured by gel permeation chromatography (GPC) using a polystyrene standard of known molecular weight as a calibration standard. The overall equivalent ratio of all NCO groups to all OH groups, i.e. NCO/OH is generally from about 0.1 to about 10, desirably from about 0.4 to about 4 and preferably from about 0.8 to about 2.2.

ADDITIVES, ETC.

In addition to the above-identified components, the polyurethane compositions of the present invention can also contain various additives, fillers, lubricants, UV absorbers, waxes, antioxidants, wetting agents, surfactants, thickening agents and the like, which can be utilized in conventional amounts as known to the art and to the literature. The additives utilized generally impart desired properties to the thermoplastic polyurethanes. Examples of fillers include talc, silicates, clays, calcium carbonate, and the like. If it is desired that the polyurethane compositions of the present invention have a color or hue, any conventional pigment or dye can be utilized in conventional amounts. Hence, any pigment known to the art and to the literature can be utilized as for example titanium dioxide, iron oxide, carbon black, and the like, as well as various dyes provided that they do not interfere with or are added after the urethane reactions are essentially complete.

Thermoset or crosslinked polymers can be obtained by using multi-functional crosslinking agents customary in the industry, such as, for example, water-soluble or water-emulsifiable melamine or benzoguans/nine resins, low viscosity polyisocyanates, polycarbodiimides, water-emulsifiable polyisocyanates or water-emulsifiable prepolymers having terminal isocyanate groups, water-soluble or water-dispersible polyaziridines, poly-epoxy functional compounds, epoxy-silanes and blocked polyisocyanates, which can be added during formulation of water-dilutable coatings, adhesives and sealants using the polyacrylic-urethane dispersions according to the invention.

The thiocarbonate-polyurethane polymers of the present invention, generally regardless of route preparation, have good properties such as toughness, abrasion resistance, good cold flexibility, excellent hydrolytic stability, good UV weatherability, good heat stability, as well as good oxidative stability and chemical resistance. However, desirably the thiocarbonyl groups are deactivated before any end use. The amount of the various vinyl monomers such as acrylate or styrene utilized will also affect the physical properties and low amount of vinyl monomers such as the various acrylates with high amounts of the thiocarbonate compounds can be utilized, or visa versa.

Utility

The bulk thermoplastic polyurethanes can be extruded into any desired end product or form, or can be cooled and pelletized or granulated for storage or bulk shipping. The extrudate can be immediately processed in any manner such as molding, injection molding, calendaring, etc.

The polyurethane dispersions obtained by the method of the invention can be employed as coating compositions and may be applied to any substrate including wood, metals, glass, cloth, leather, paper, plastics, foam and the like, by any conventional method including brushing, dipping, flow coating, spraying and the like. Films obtained from the coating compositions can be used as adhesives in the production of composite articles.

Coatings with regard to various wood substrates are preferred. However, the polyurethanes can also be used to coat fabrics, either woven or non-woven and made from polyester fibers, polyolefin fibers, nylon fibers, or natural fibers and the like. Industrial applications include coated films, sheets, or fabrics as for conveyer belts, containers, collapsible storage bags (e.g., fuel, water, fruit juices, food oils, heating oils etc), inflatables (e.g., escape slides and platforms, flotation devices, air-mattresses, life jackets, white-water or life rafts, oil booms, petro-seals, power lifting devices, weather balloons) or grape press membranes, and the like.

In the apparel industry, uses include labels and stickers used in laundry and professional outfits, as well as protective clothing/apparel, protective covers, rainwear, sealable coatings for labels, surgical drapes, protective apparel, synthetic leather, tents, upholstery, wet or diving suits, and the like. Other uses include liners for pipe repair, load space covers, and the like or any application where melt processable materials are used. The polyurethanes are also useful is sealant, caulking, adhesive, and other elastomeric applications.

An important area of use of the waterborne polyurethane dispersions of the present invention is in the personal care field and cosmetic field such as for film formers to provide water or moisture resistance, luster, better spreadability of solutions, and the like. Such dispersions can be incorporated as a component thereof into personal care products such as daily skin care products (cosmetics, lip balms, moisturizers, eye-lash liners, lipsticks, lip balms, sunscreens, and the like), as well as nail care products, hair care products, and the like. Such personal care products can be lotions, gels, sprays, sticks, compressed liquids, liquid suspensions, and the like. The urethane dispersions of the present invention are especially suitable as hair fixatives, nail polish, and the like.

Personal care compositions can include the waterborne polyurethane dispersions of this invention, mixed and optionally reacted further with a topically acceptable phase. The term "topically acceptable phase" means any combination of optional liquid or solid ingredients suitable for a desired personal care composition in combination with (and sometimes reacted with) the plasticized waterborne polyurethane dispersions described heretofore. Such optional ingredients can comprise one or more of a wide variety of components well known to those skilled in the art, such as chelators, conditioners, diluents, fragrances, humectant skin or hair conditioners, lubricants, moisture barriers/emollients, neutralizers, opacifiers, pharmaceutical actives, preservatives, solvents, spreading aids, sunscreens, surfactants, conditioning polymers, vitamins, viscosity modifiers/emulsifiers, and the like, as well as numerous other optional components for enhancing and maintaining the properties of the personal care compositions. Exemplary skin care compositions utilizing such components include those of U.S. Pat. Nos. 5,073,372, 5,380,528, 5,599,549, 5,874,095, 5,883,085, 6,013,271, and 5,948,416, all incorporated herein by reference. Such components are also described in detail in well known references such as Mitchell C. Schlossman, The Chemistry and Manufacture of Cosmetics, Volumes 1 and 11, Allured Publishing Corporation, 2000.

The polyurethanes can also be used to make unsupported TPU film and sheet via extrusion or calendering. Applications for such films and sheets include air mattresses, shower curtains, aeration sheets for water purification plants, adhesives, equipment covers, protective wear, aprons, body bags, tank liners, pipe liners, and the like. The polyurethanes can be formed into articles comprising films, membranes or sheets which range generally from about 0.25 or about 0.50 mils to about 10 mils (about 6.35 or about 12.7 to about 254 micrometers), and preferably from about 1 mil to about 4 mils (about 25.4 to about 101.6 micrometers).

While in accordance with the patent statutes the best mode and preferred embodiment have been set forth, the scope of the invention is not intended to be limited thereto, but only by the scope of the attached claims.

What is claimed is:

1. A hydroxyl-terminated thiocarbonate represented by a compound of the formula:

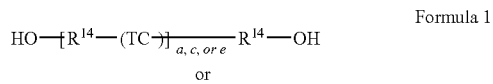

Formula 1 or

Formula 2 wherein $R^{14}$ is a polyol residue, wherein said polyol is selected from a hydrocarbon polyol wherein $R^{14}$ is selected from a substituted or unsubstituted alkylene group having from 2 to about 200 carbon atoms, and wherein said substituted alkylene group having a substituent selected from a halide and cyano; a polyester polyol, polyether polyol, polyhydroxy polyester amide, a polycaprolactone having a hydroxyl group, an epoxide having a hydroxyl group, polyhydroxy polycarbonate, polyhydroxy polyacetal, polyhydroxy polythioether, polysiloxane polyol, ethoxylated polysiloxane polyol, polybutadiene polyol, hydrogenated polybutadiene polyol, polyacrylate polyol, halogenated polyester polyol, halogenated polyether polyol, and combinations thereof;

wherein said —$R^{14}$-(TC)— of Formula 1 is represented by the formula:

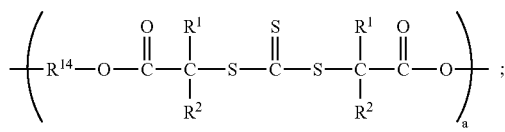

wherein a is from 1 to about 20, wherein $R^1$ and $R^2$, independently, are selected from substituted and unsubstituted linear and branched alkyl having from 1 to about 6 carbon atoms, and substituted or unsubstituted aryl having from 1 to 6 substituents on the aryl ring; wherein said substituents on said substituted alkyl and on said substituted aryl groups, independently, are selected from an alkyl having from 1 to 6 carbon atoms, aryl, halogen, cyano, an ether having a total of from 2 to about 20 carbon atoms, nitro, and combinations thereof; and $R^1$ and $R^2$ are part of a cyclic ring having from about 5 to about 12 total carbon atoms; or wherein said —$R^{14}$-(TC)— of Formula 1 is represented by the formula:

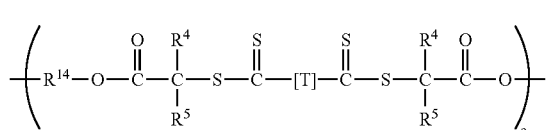

wherein c is from 1 to about 20; wherein $R^4$ and $R^5$, independently, are selected from substituted and unsubstituted linear and branched alkyl having from 1 to about 12 carbon atoms; substituted and unsubstituted aryl having from 6 to about 18 carbon atoms; $R^4$ and $R^5$ can form a substituted and unsubstituted cyclic ring having from 3 to about 12 carbon atoms; wherein when $R^4$ and $R^5$ are substituted said substituents, independently, are selected from an alkyl having from 1 to 6 carbon atoms, aryl, halogen, cyano, an ether having a total of from 2 to about 20 carbon atoms, nitro, and combinations thereof; and T is a divalent radical having a nitrogen atom directly connected to a thiocarbonyl group and is represented by the formula:

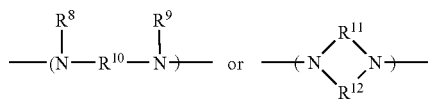

wherein $R^8$ and $R^9$, independently, are selected from hydrogen, substituted and unsubstituted linear or branched alkyl having from 1 to about 18 carbon atoms, substituted and unsubstituted aryl having from about 6 to about 18 carbon atoms, substituted and unsubstituted arylalkyl having from 7 to about 18 carbon atoms, substituted and unsubstituted alkenealkyl having from 3 to about 18 carbon atoms, wherein when $R^8$ and $R^9$ are substituted the substituents are selected from an alkyl having, from 1 to 6 carbon atoms, aryl, halogen which can be the same or different, cyano, an ether having a total of from 2 to about 20 carbon atoms, nitro, and combinations thereof;

wherein $R^{10}$ is present or not present and is selected from a substituted and unsubstituted alkylene group having from 1 to about 18 carbon atoms, a substituted and unsubstituted polyalkylene glycol ether residue having from 3 to about 200 carbon atoms, wherein when $R^{10}$ is substituted the substituents are selected from an alkyl having from 1 to 6 carbon atoms, aryl, halogen which can be the same or different, cyano, an ether having a total of from 2 to about 20 carbon atoms, nitro, and combinations thereof; and wherein $R^{11}$ and $R^{12}$, independently, are selected from a substituted and unsubstituted alkylene group having from 1 to 4 carbon atoms, with $R^{11}$ and $R^{12}$ having a total of from about 3 to about 5 carbon atoms, wherein when $R^{11}$ and $R^{12}$ are substituted the substituents are selected from an alkyl having from 1 to 6 carbon atoms, aryl, halogen which can be the same or different, cyano, an ether having a total of from 2 to about 20 carbon atoms, nitro, and combinations thereof; and wherein said —$R^{14}$-(TC)— of Formula 1 is represented by the formula:

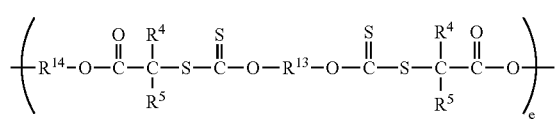

wherein e is from 1 to about 20; wherein $R^4$ and $R^5$, independently, are defined as set forth above; wherein $R^{13}$ is selected from a substituted or unsubstituted linear or branched alkylene having from 1 to about 12 carbon atoms, aryl, a polyalkylene glycol residue; wherein when $R^{13}$ substituted said substituents are selected from an alkyl having from 1 to 6 carbon atoms, aryl, halogen, a cyano group, an amino group, an alkene group, an alkoxycarbonyl group, an aryloxycarbonyl group, a carboxy group, an acyloxy group, a carbarnoyl group, an alkylcarbonyl group, an alkylarylcarbonyl group, an arylcarbonyl group, an arylalkylcarbonyl group, a phthalimido group, a maleimido group, a succinimido group, amidino group; guanidimo group, allyl group, epoxy group, alkoxy group, an alkali metal salt, a quaternary ammonium salt, a hydroxyl group, nitro, a carboalkoxy group and combinations thereof; or wherein said TC of Formula 2 is represented by the formula:

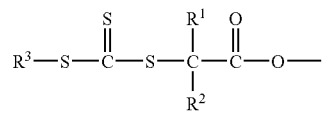

wherein $R^3$ is selected from benzyl, a substituted and unsubstituted $C_1$ through $C_{18}$ alkyl, wherein said substituent when present is selected from halogen, hydroxyl, alkoxy, a $C_1$ to $C_{18}$ hydroxyalkyl, aralkyl, cyanoalkyl, aminoalkyl, carboxylalkyl, carboalkoxyalkyl, and mercaptoalkyl; and wherein $R^1$ and $R^2$, independently, are defined as set forth above; or wherein TC of Formula 2 is represented by the formula:

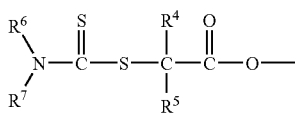

wherein $R^4$ and $R^5$, independently, are defined as set forth above; and wherein $R^6$ and $R^7$, independently, are selected from hydrogen, a substituted and unsubstituted linear and branched alkyl having from 1 to about 18 carbon atoms, a substituted and unsubstituted aryl having from 6 to about 18 carbon atoms optionally saturated or unsaturated, a substituted and unsubstituted arylalkyl having from about 7 to about 18 carbon atoms, a substituted and unsubstituted alkenealkyl having from 3 to about 18 carbon atoms, a polyalkylene glycol ether residue having from 3 to about 200 carbon atoms, piperazine, morpholine, pyrrolidone, piperidine, 4-alkyl amino-2,2,6,6-tetramethyl piperidine, 1-alkylamioalkyl-3,3,5,5-tetramethyl-2-piperazinone, hexamethyleneimine, phenothiazine, iminodibenzyl, phehoxazine, N,N'-diphenyl-1,4-phenylenediarnine, and dicyclohexylamine, or $R^6$ and $R^7$ can form a substituted or unsubstituted cyclic ring having a total of from 4 to about 12 carbon atoms; and wherein when said $R^6$ and $R^7$ are substituted said substituents, independently, are selected from an alkyl having from 1 to 6 carbon atoms, aryl, halogen, a cyano group, an amino group, an alkene group, an alkoxycarbonyl group, an aryloxycarbonyl group, a carboxy group, an acyloxy group, a carbamoyl group, an alkylcarbonyl group, an alkylarylcarbonyl group, an arylcarbonyl group, an arylalkylcarbonyl group, a phthalimido group, a maleimido group, a succinimido group, amidino group; guanidimo group, allyl group, epoxy group, alkoxy group, an alkali metal salt, a quaternary ammonium salt, a hydroxyl group, an ether having a total of from 2 to about 20 carbon atoms, a nitro, a carboalkoxy group, and combinations thereof; or wherein said TC of Formula 2 is represented by the formula:

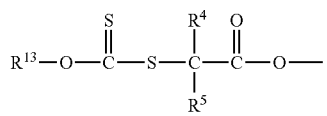

wherein $R^4$ and $R^5$, independently, are defined as set forth above; and wherein $R^{13}$ is optionally substituted and is selected from a linear and branched alkyl having from 1 to about 12 carbon atoms, aryl, arylalkyl having from about 7 to about 18 carbon atoms, acyl, alkenealkyl having from 3 to about 18 carbon atoms, a polyalkylene glycol residue, a polyalkylene glycol monoalkyl ether residue having from about 3 to about 200 carbon atoms, a polyalkylene glycol monoaryl ether residue having from about 3 to about 200 carbon atoms; wherein when said $R^{13}$ is substituted said substituents, independently, are selected from an alkyl having from 1 to 6 carbon atoms, aryl, halogen, a cyano group, an amino group, an alkene group, an alkoxycarbonyl group, an aryloxycarbonyl group, a carboxy group, an acyloxy group, a carbamoyl group, an alkylcarbonyl group, an alkylarylcarbonyl group, an arylcarbonyl group, an arylalkylcarbonyl group, a phthalimido group, a maleimido group, a succinimido group, amidino group; guanidimo group, allyl group, epoxy group, alkoxy group, an alkali metal salt, a quaternary ammonium salt, a hydroxyl group, an ether having a total of from 2 to about 20 carbon atoms, a nitro, a carboalkoxy group, and combinations thereof.

2. The hydroxyl-terminated thiocarbonate according to claim 1, wherein $R^1$ and $R^2$, independently, are selected from methyl, and phenyl, wherein $R^3$ is an alkyl having from 1 to about 18 carbon atoms; wherein $R^4$ and $R^5$, independently, are selected from methyl and phenyl.

3. The hydroxyl-terminated thiocarbonate according to claim 2, wherein $R^6$ and $R^7$, independently, are selected from a phenyl, an alkyl, and a substituted alkyl having from 1 to about 18 carbon atoms.

4. The hydroxyl-terminated thiocarbonate according to claim 3, wherein $R^6$ and $R^7$ are selected from methylene and hexamethylene.

5. The hydroxyl-terminated thiocarbonate according to claim 1, wherein said polyol is said hydrocarbon polyol.

6. The hydroxyl-terminated thiocarbonate according to claim 2, wherein said polyol is said hydrocarbon polyol and wherein said alkyl or alkylene group, or said substituted alkyl or alkylene group has from 2 to about 10 carbon atoms.

7. The hydroxyl-terminated thiocarbonate according to claim 4, wherein said polyol is selected from ethylene glycol, diethylene glycol, propylene glycol, trimethyloipropane, butylene glycol, hexane diol, neopentyl glycol, polytetrahydrafuran, and combinations thereof.

8. The hydroxyl-terminated thiocarbonate according to claim 1, wherein said TC of Formula 2 is represented by the formula:

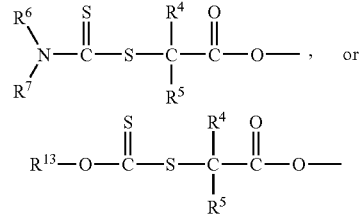

and wherein said polyol is said hydrocarbon polyol and wherein said alkylene group, or said substituted alkylene group has from 2 to about 10 carbon atoms.

9. The hydroxyl-terminated thiocarbonate according to claim 7, wherein said TC of Formula 2 is represented by the formula:

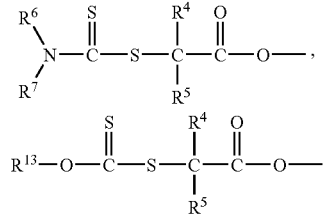

and wherein said polyol is selected from ethylene glycol, diethylene glycol, propylene glycol, trimethylolpropane, butylene glycol, hexane diol, neopentyl glycol, polytetrahydrafuran, and combinations thereof.

* * * * *

UNITED STATES PATENT AND TRADEMARK OFFICE
CERTIFICATE OF CORRECTION

| | | |
|---|---|---|
| PATENT NO. | : 7,557,235 B2 | Page 1 of 1 |
| APPLICATION NO. | : 10/913972 | |
| DATED | : July 7, 2009 | |
| INVENTOR(S) | : John Ta-Yuan Lai et al. | |

It is certified that error appears in the above-identified patent and that said Letters Patent is hereby corrected as shown below:

Title page item [60] under Related U.S. Application Data the last 3 lines of the patent should be deleted to read:
--Continuation-in-part of application No. 10/681,679, filed on Oct. 8, 2003, now Pat. No. 7,335,788, which is a continuation-in-part of application No. 10/278,335, filed on Oct. 23, 2002, now Pat. No. 7,205,368, which is a continuation-in-part of application No. 09/505,749, filed on Feb. 16, 2000, now Pat. No. 6,596,899.--.

In column 52, line 28, claim 7 the term "trimethyloipropanc" should be changed to --trimethylolpropane--.

In column 52, about line 54, claim 9 the term --or-- should be inserted after the formula.

Signed and Sealed this

Twenty-fifth Day of August, 2009

David J. Kappos
*Director of the United States Patent and Trademark Office*